(12) United States Patent
Horigome et al.

(10) Patent No.: US 10,551,315 B2
(45) Date of Patent: Feb. 4, 2020

(54) FLUORESCENCE SPECTROPHOTOMETER AND FLUORESCENCE SPECTROMETRY AND IMAGING METHOD

(71) Applicant: HITACHI HIGH-TECH SCIENCE CORPORATION, Tokyo (JP)

(72) Inventors: Jun Horigome, Tokyo (JP); Rino Nakajima, Tokyo (JP); Yoichi Sato, Tokyo (JP)

(73) Assignee: HITACHI HIGH-TECH SCIENCE CORPORATION, Tokyo (JP)

( * ) Notice: Subject to any disclaimer, the term of this patent is extended or adjusted under 35 U.S.C. 154(b) by 0 days.

(21) Appl. No.: 16/041,661

(22) Filed: Jul. 20, 2018

(65) Prior Publication Data

US 2019/0025208 A1 Jan. 24, 2019

(30) Foreign Application Priority Data

Jul. 21, 2017 (JP) .................... 2017-141929

(51) Int. Cl.
*G01J 3/30* (2006.01)
*G01N 21/64* (2006.01)
(Continued)

(52) U.S. Cl.
CPC .......... *G01N 21/64* (2013.01); *G01N 21/25* (2013.01); *G01N 21/47* (2013.01); *G01N 2021/6421* (2013.01); *G01N 2021/6439* (2013.01)

(58) Field of Classification Search
CPC ...... G01N 21/64; G01N 21/645; G01N 21/25; G01N 21/47; G01N 2021/6417;
(Continued)

(56) References Cited

U.S. PATENT DOCUMENTS 5,317,378 A * 5/1994 Mould .................. G01N 21/03
356/236
6,020,959 A 2/2000 Imura
(Continued)

FOREIGN PATENT DOCUMENTS

JP 2003232683 A 8/2003
JP 2005319211 A 11/2005
(Continued)

OTHER PUBLICATIONS

European Patent Office, "Extended European Search Report", issued in connection with European Patent Application No. 18184562.9, dated Dec. 10, 2018 (10 pages).

*Primary Examiner* — Tarifur R Chowdhury
*Assistant Examiner* — Jonathon Cook
(74) *Attorney, Agent, or Firm* — Holland & Hart LLP

(57) ABSTRACT

A fluorescence spectrophotometer includes: a light source; an excitation side spectroscope configured to separate light from the light source to generate excitation light; an integrating sphere having an inner surface configured to scatter the excitation light that has entered the integrating sphere; a sample holder, which is provided at a position on the integrating sphere that is not directly irradiated with the excitation light that has entered the integrating sphere and that is capable of being irradiated with the excitation light that has been scattered by the inner surface, and which is capable of holding a sample to be measured; a detector configured to detect fluorescent light emitted from the sample irradiated with the excitation light that has been scattered by the inner surface; and an imaging device configured to take the sample image of the sample that emits the fluorescent light.

7 Claims, 25 Drawing Sheets

(51) Int. Cl.
*G01N 21/25* (2006.01)
*G01N 21/47* (2006.01)

(58) Field of Classification Search
CPC ... G01N 2021/6419; G01N 2021/6421; G01N 2021/6439; G01N 2201/065; G01J 3/0254
USPC ............................... 356/317, 331, 333, 334
See application file for complete search history.

(56) References Cited

U.S. PATENT DOCUMENTS

| | | | |
|---|---|---|---|
| 6,583,879 B1 | 6/2003 | Berg et al. | |
| 6,917,429 B2 * | 7/2005 | Imura | G01J 3/0251 |
| | | | 250/214 R |
| 7,812,952 B2 * | 10/2010 | Delaage | G01N 21/6452 |
| | | | 356/417 |
| 8,462,337 B2 * | 6/2013 | Watanabe | G01J 3/02 |
| | | | 356/317 |

FOREIGN PATENT DOCUMENTS

| | | | |
|---|---|---|---|
| JP | 2007515640 A | 6/2007 | |
| JP | 2008261885 A | 10/2008 | |
| JP | 20009008509 A * | 1/2009 | ............ G01J 3/0254 |
| JP | 2013-137199 A | 7/2013 | |
| JP | 2016151426 A | 8/2016 | |
| WO | WO2017/056830 A1 | 4/2017 | |

* cited by examiner

SAMPLE IMAGE LIST

FLUORESCENCE SPECTROPHOTOMETER AND FLUORESCENCE SPECTROMETRY AND IMAGING METHOD

CROSS REFERENCE TO RELATED APPLICATION

This application claims priority to and the benefit of Japanese Patent Application No. 2017-141929, by HORIGOME et al., filed Jul. 21, 2017, which is hereby incorporated by reference in its entirety into this application.

BACKGROUND OF THE INVENTION

1. Field of the Invention

The present invention relates to a fluorescence spectrophotometer and a fluorescence spectrophotometry and imaging method.

2. Description of the Related Art

There has been known a fluorescence spectrophotometer, which is configured to analyze a sealed material or liquid enclosed (contained) in a sample container ("Fluorometry—Applications to Biological Science", The Spectroscopical Society of Japan —Measurement Method Series 3, pp. 45-77, Japan Scientific Societies Press, Jan. 20, 1983 (hereinafter referred to as "Non-patent Document 1")). There has also been known a fluorescence spectrophotometer, which uses an integrating sphere to correct a fluorescence spectrum ("A Simple Correction Method for Determination of Absolute Fluorescence Quantum Yields of Solid Samples with a Conventional Fluorescence Spectrophotometer", Japan analyst, Volume 58, Issue 6, pp. 553-559, 2009 (hereinafter referred to as "Non-patent Document 2")). There has further been known a fluorescence fingerprint imaging device to which a technology of spectral imaging for acquiring a spectral image is applied ("Development of the Fluorescence Fingerprint Imaging Technique", Journal of the Japanese Society for Food Science and Technology, Volume 62, Issue 10, 2015 (hereinafter referred to as "Non-patent Document 3")).

There has been known a fluorescence detection device configured to detect fluorescence of a sample by using, as a light source, an LED that emits single-wavelength excitation light (WO 2017/056830 A1 (hereinafter referred to as "Patent Document 1")). There has also been known a device configured to acquire fluorescence spectrum information in each pixel of an image by using a hyperspectral camera (Japanese Patent Application Laid-open No. 2013-137199 (hereinafter referred to as "Patent Document 2")).

Such a fluorescence photometer as described in Non-patent Documents 1 and 2 acquires, as an excitation spectrum, a fluorescence spectrum obtained when a sample is placed and irradiated with excitation light or a fluorescence intensity obtained when a wavelength of the excitation light is changed. At this time, a sample chamber is required to be a dark room, and hence an emission distribution, an emission color, an emission intensity, and other such states of fluorescence of the sample at the time of being irradiated with the excitation light cannot be identified.

Meanwhile, such a fluorescence fingerprint imaging device as described in Non-patent Document 3 acquires emission information of fluorescence as an image of an in-plane distribution. With this method, fluorescence information obtained when the sample is irradiated with freely-selected excitation light can be acquired as the image. At this time, white light is separated by optical filters, and hence an excitation wavelength is limited by the number of optical filters. Moreover, the sample is directly irradiated with the excitation light through a lens, and hence an excitation light irradiation density is biased toward a center portion, with the result that an amount of excitation light becomes uneven. The amount of excitation light and the fluorescence intensity are in a proportional relationship, and hence the unevenness in amount of light may lead to an uneven fluorescence image in the plane of the sample.

In Patent Document 1, as in Non-patent Document 3, there is acquired image data focusing attention on fluorescence generated under the state in which the sample is irradiated with the excitation light. In Patent Document 1, an LED having a single emission wavelength is used as the light source of the excitation light. A plurality of LEDs as the light sources of the excitation light may be prepared depending on samples to excite the samples with different excitation wavelengths, but the excitation wavelengths are limited to the number of LEDs. Moreover, in Non-patent Document and Patent Document 1, the emission information of the fluorescence is acquired as the image of the in-plane distribution. However, a fluorescence spectrum cannot be acquired, and an intensity of the fluorescence is merely grasped in the image.

With the device described in Patent Document 2, the fluorescence spectrum information in each pixel in the image can be acquired with the use of the hyperspectral camera. However, the hyperspectral camera is expensive, and a data acquisition interval of the spectrum has a resolution that is as low as about 5 nm. Moreover, the sample is directly irradiated with the excitation light, with the result that the amount of excitation light becomes uneven, and hence a sample image in the plane of the sample may become uneven.

Moreover, as described in Non-patent Document 3, in a related-art measurement site, it is common to acquire spectral information with the fluorescence photometer, and narrow down excitation and fluorescence wavelength conditions based on the information to acquire a sample image of fluorescence. Therefore, it is a common method to display information of the spectrum and the sample image separately and independently.

In other words, it is common to acquire the information of the spectrum and the sample image with different devices, and to display the information separately. The spectrum is, so to speak, average information obtained by averaging the entire region irradiated with light, and for a sample having uneven properties for each region, it has been difficult to identify such unevenness. Meanwhile, information on such unevenness can be obtained from the sample image, but it has been difficult to check the information along with the spectrum indicating the overall properties. It is desired to measure the sample taking in consideration both the spectrum indicating the overall properties of the sample and the sample image indicating the properties of each region of the sample. It is true not only for the fluorescence photometer but also for other photometric analyzers.

SUMMARY OF THE INVENTION

The present invention relates to a fluorescence spectrophotometer, which is capable of realizing accurate and convenient sample measurement, and to a fluorescence spectrophotometry and imaging method.

According to one embodiment of the present invention, there is provided a fluorescence spectrophotometer including: a light source; an excitation side spectroscope, which is configured to separate light from the light source to generate excitation light; an integrating sphere, which has an inner surface configured to scatter the excitation light that has entered the integrating sphere; a sample holder, which is provided at a position on the integrating sphere that is not directly irradiated with the excitation light that has entered the integrating sphere and that is capable of being irradiated with the excitation light that has been scattered by the inner surface, and which is capable of holding a sample to be measured; a detector, which is configured to detect fluorescent light emitted from the sample irradiated with the excitation light that has been scattered by the inner surface; and an imaging device, which is configured to take a sample image of the sample that emits the fluorescent light.

According to the present invention, the sample can be irradiated with excitation light with reduced unevenness, and fluorescent light with reduced unevenness can be extracted, with the result that excellent sample images and spectra can be acquired at the same time. Further, according to the present invention, such a sample image and such a spectrum can be displayed in the same screen, and hence the convenience is increased.

BRIEF DESCRIPTION OF THE DRAWINGS

FIG. 5A and FIG. 5B are graphs for showing three-dimensional spectra, of which FIG. 5A is a graph for showing a three-dimensional fluorescence spectrum of an excitation wavelength, a fluorescence wavelength, and a fluorescence intensity, and FIG. 5B is a graph for showing a three-dimensional time-varying spectrum of time, the fluorescence wavelength, and the fluorescence intensity.

FIG. 6A and FIG. 6B are views for illustrating a configuration of an example of an integrating sphere, of which FIG. 6A is a top view, and FIG. 6B is a side view.

FIG. 25A and FIG. 25B are views for illustrating a configuration of another example of the integrating sphere, of which FIG. 25A is a top view, and FIG. 25B is a side view.

DESCRIPTION OF THE EMBODIMENTS

Now, fluorescence spectrophotometers according to exemplary embodiments of the present invention are described in detail with reference to FIG. 1 to FIG. 26.

Figure 1:
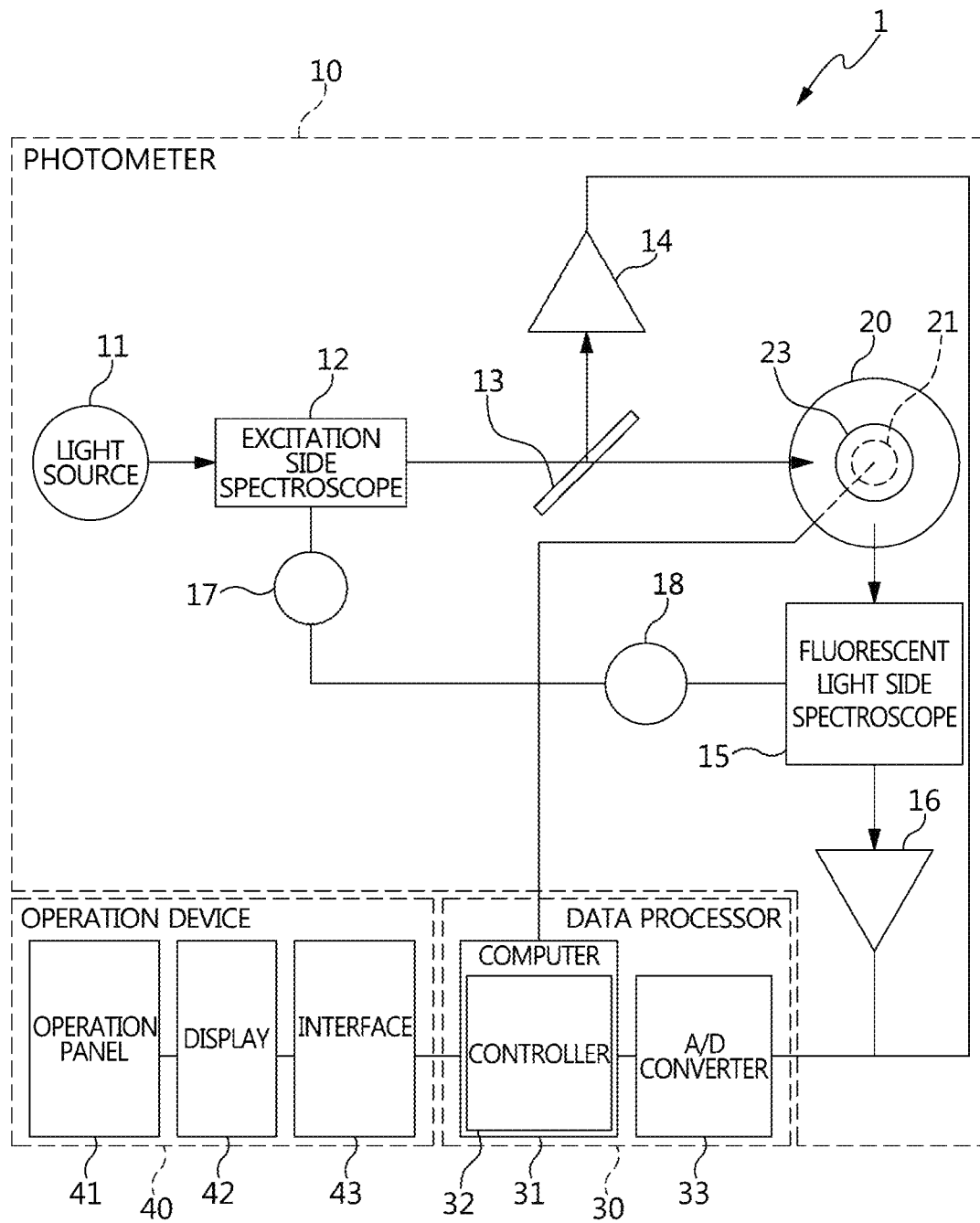
FIG. 1 is a configuration block diagram for illustrating a fluorescence spectrophotometer according to an embodiment of the present invention.

FIG. 1 is a configuration block diagram for illustrating a fluorescence spectrophotometer according to an embodiment of the present invention. A configuration of the fluorescence spectrophotometer of this embodiment is described in detail with reference to FIG. 1.

A fluorescence spectrophotometer 1 according to this embodiment is a device configured to irradiate a sample with excitation light to measure fluorescent light emitted from the sample, and includes a photometer 10, a data processor 30, which is arranged in the photometer 10, and is configured to control the photometer 10 to analyze the sample, and an operation device 40, which is used for input and output.

The photometer 10 includes a light source 11, an excitation side spectroscope 12, which is configured to separate light from the light source 11 to generate the excitation light, a beam splitter 13, which is configured to separate light from the excitation side spectroscope 12, a monitor detector 14, which is configured to measure an intensity of a partial light that is separated by the beam splitter 13, a fluorescent light side spectroscope 15, which is configured to separate the fluorescent light emitted from the sample into monochromatic light, a detector (fluorescence detector) 16, which is configured to detect an electrical signal of the monochromatic fluorescent light, an excitation side pulse motor 17, which is configured to drive a diffraction grating of the excitation side spectroscope 12, and a fluorescent light side pulse motor 18, which is configured to drive a diffraction grating of the fluorescent light side spectroscope 15.

The data processor 30 includes a computer 31, a controller 32, which is arranged in the computer 31, and an A/D converter 33 configured to convert the fluorescent light from the sample into a digital signal. Moreover, the operation device 40 includes an operation panel 41, to which an operator inputs an input signal that is required for processing by the computer 31, a display 42, which is configured to display various analysis results processed by the computer 31, and an interface 43, which is configured to connect the operation panel 41 and the display 42 to the computer 31.

Based on measurement conditions input to the operation panel 41 by the operator, the computer 31 outputs a signal to the excitation side pulse motor 17, and the excitation side pulse motor 17 is driven to set the excitation side spectroscope 12 to a target wavelength position. Similarly, based on the measurement conditions, the computer 31 outputs a signal to the fluorescent light side pulse motor 18, and the fluorescent light side pulse motor 18 is driven to set the fluorescent light side spectroscope 15 to a target wavelength position. Each of the excitation side spectroscope 12 and the fluorescent light side spectroscope 15 has a diffraction grating having a predetermined slit width, a prism, and other such optical elements, and the optical elements are moved to rotate with the excitation side pulse motor 17 and the fluorescent light side pulse motor 18 serving as powers via gears, cams, and other such drive system parts to enable spectral scanning.

The photometer 10 further includes an integrating sphere 20. The integrating sphere 20 exhibits a substantially spherical shape with no substance existing inside thereof to define an interior space. Moreover, the integrating sphere 20 includes a sample holder 23, which is capable of holding (containing or enclosing) a sample to be measured, which takes various forms, such as solid, powder, and liquid. The sample holder 23 is configured to be removable from the integrating sphere 20, exhibits a circular plate shape, and holds the sample with spring stress.

Further, in this embodiment, a camera module (imaging device) 21 is provided in the vicinity of the integrating sphere 20. In contrast to the detector 16, which is configured to detect the electrical signal of the fluorescent light from the sample to acquire an intensity of a spectrum, the camera module 21 is configured to take and acquire a sample image (image of a sample surface) with the fluorescent light from the sample. In this embodiment, the sample holder 23 is placed at a position at which the sample is not directly irradiated with the partial excitation light that is separated by the beam splitter 13. Meanwhile, the camera module 21 is placed at a position that is opposite to (including the vicinity of the position that is opposite to) the position of the sample holder 23 when viewed from a center of the integrating sphere 20 to image the surface of the sample based on the fluorescent light emitted by the sample irradiated with the light from the light source 11.

The integrating sphere 20 takes in the partial excitation light that is separated by the beam splitter 13. On an inner surface (that defines the interior space) of the integrating sphere 20, a highly reflective white material, for example, barium sulfate, is applied. The integrating sphere 20 reflects and scatters, on the inner surface, the excitation light that has entered the integrating sphere 20 to irradiate the sample held in the sample holder 23 with averaged excitation light. Further, the fluorescent light emitted from the sample is reflected and scattered by the inner surface of the integrating sphere 20, exits from the integrating sphere, and is guided to the fluorescent light side spectroscope 15 and the detector 16.

In a case of a surface photometric optical system, the surface of the sample may be rough or uneven to highly and unevenly scatter light in some cases, and hence there is a possibility that different results are obtained depending on how the sample is set, that is, placement reproducibility is reduced to result in a variation in data. For example, there is a possibility that the way the sample is set may be slightly different for each operator.

With the use of the integrating sphere 20, even when an illumination intensity of the light source 11 may be uneven, the excitation light that has entered the integrating sphere 20 is reflected and scattered by the inner surface to be averaged and reduced in unevenness. It is desired to adopt an arrangement with which the irradiation light from the light source 11 is prevented from directly entering the sample surface, the detector, and the camera. In a method of use of the integrating sphere 20 in the related art, the number of times of reflection in the integrating sphere 20 is increased depending on the arrangement of the light source, a baffle, and the detector to attenuate the irradiation light, and there is a possibility that a fluorescence intensity from the sample surface may be weakened as a result. With the arrangement in this embodiment, the attenuation of the irradiation light is also suppressed, and a sufficient intensity of the excitation light can be obtained. The sample held in the sample holder 23 is irradiated with this excitation light with reduced unevenness. Further, the fluorescent light emitted from the sample is reflected and scattered by the inner surface of the integrating sphere 20 to have an even intensity, and fluorescent light with reduced unevenness can be obtained irrespective of how the sample is placed. Details of the integrating sphere 20 are described later.

The emitted fluorescent light is taken in by the fluorescent light side spectroscope 15 and separated into the monochromatic light, and the monochromatic light is detected by the detector 16 and taken in as a signal intensity by the computer 31 via the A/D converter 33, with the result that the various analysis results are displayed on the display 42. Meanwhile, the emitted fluorescent light is imaged by the camera module 21, with the result that the sample image is acquired and displayed on the display 42.

Figure 2:
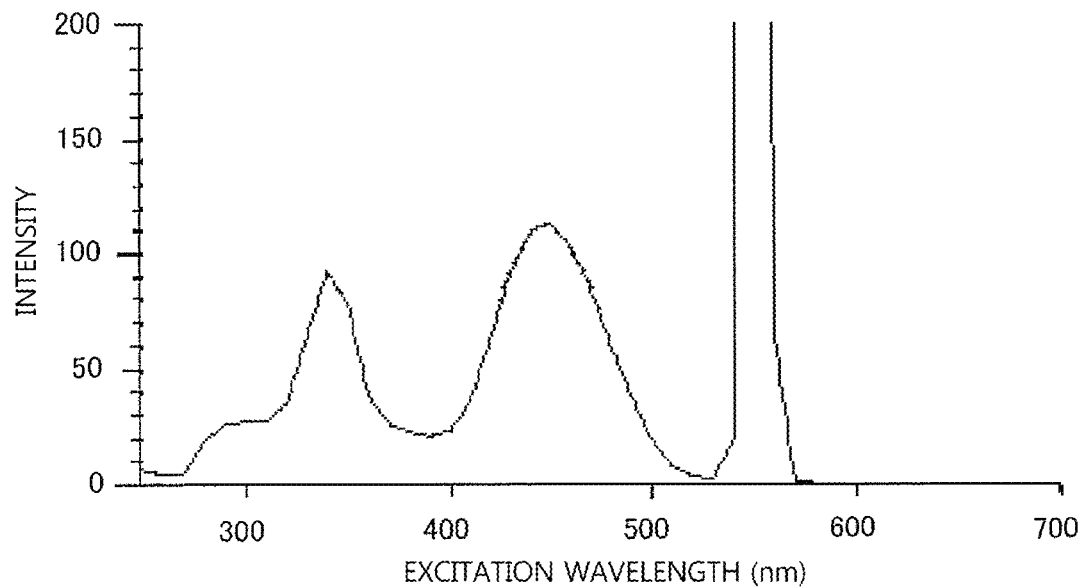
FIG. 2 is a graph for showing, in measurement by the fluorescence spectrophotometer, an excitation spectrum indicating an intensity of fluorescent light with respect to an excitation wavelength.
Figure 4:
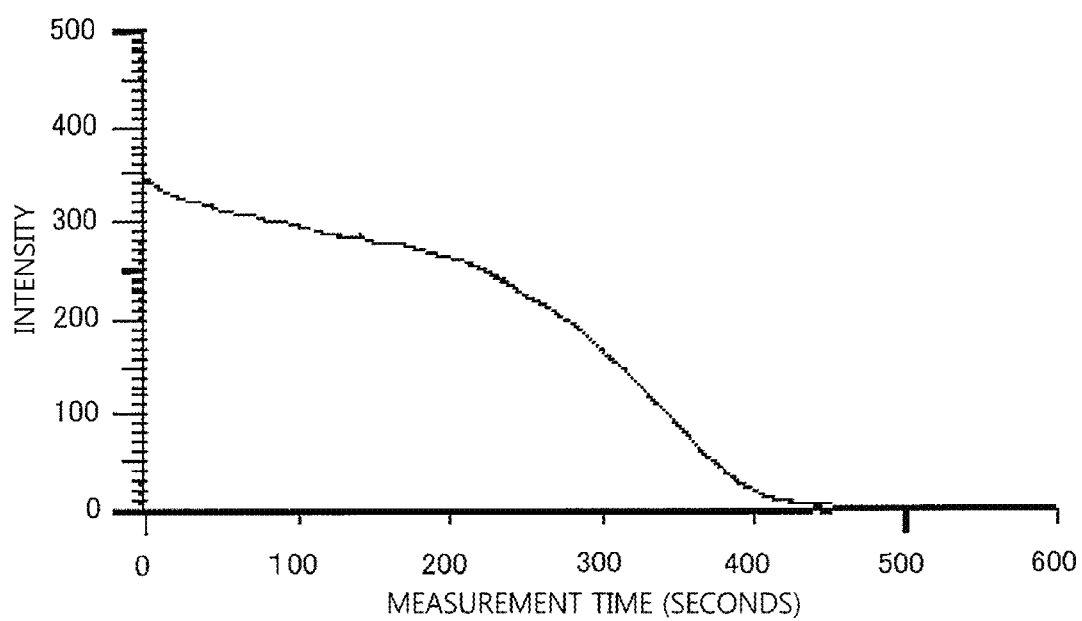
FIG. 4 is a graph for showing, in the measurement by the fluorescence spectrophotometer, a time-varying spectrum indicating an intensity of fluorescent light of a particular wavelength corresponding to excitation light of a particular wavelength.
Figure 5A:
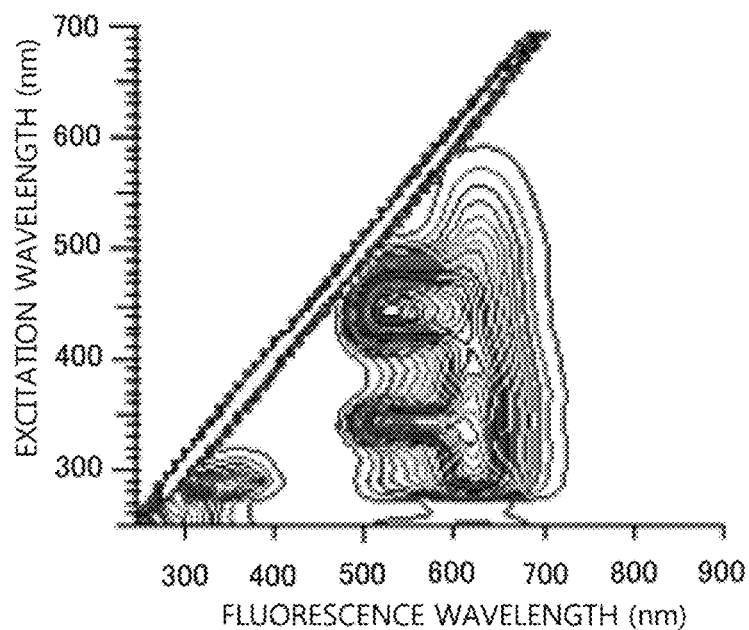
Figure 5B:
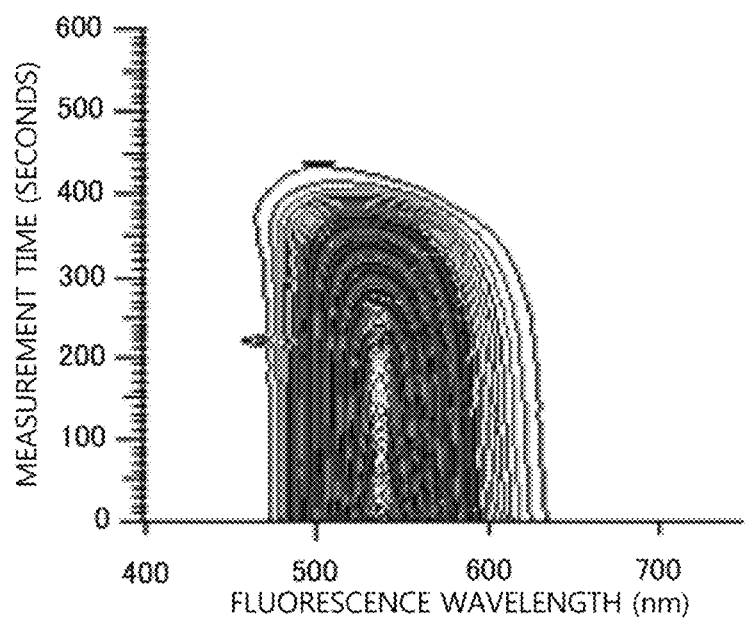

In general, the electrical signal of the fluorescent light from the sample, which is obtained from the detector 16, is displayed on the display 42 informs of various spectra indicating an intensity of the fluorescent light. In FIG. 2 to FIG. 5B, there are shown examples of a two-dimensional spectrum including two axes, which is obtained not only by the fluorescence spectrophotometer 1 according to this embodiment but also by a general fluorescence spectrophotometer. In FIG. 2, there is shown an excitation spectrum, which is an example of the spectrum, and in FIG. 3, there is shown a fluorescence spectrum, which is another example of the spectrum. In FIG. 4, there is shown a time-varying spectrum, which is still another example of the spectrum. In FIG. 5A and FIG. 5B, there are shown three-dimensional spectra, which are examples of the spectrum.

The excitation spectrum shown in FIG. 2 is a spectrum obtained by measuring the fluorescence intensity obtained when an excitation wavelength of the excitation light is changed with respect to the sample in the sample holder 23. The excitation side spectroscope 12 changes the excitation wavelength from a measurement start wavelength to a measurement end wavelength, and irradiates the sample with the excitation light of each wavelength. A change in fluorescent light of a particular wavelength is detected by the detector 16 via the fluorescent light side spectroscope 15, which is set to a fixed wavelength at the time, and is taken in as a signal intensity by the computer 31 via the A/D converter 33. The computer (controller 32) subjects the signal intensity to analysis processing to generate a spectrum that can be displayed on the display 42.

The display 42 displays, as a measurement result, such a two-dimensional excitation spectrum of the excitation wavelength and the fluorescence intensity as shown in FIG. 2. The spectrum (graph) of FIG. 2 indicates the fluorescence intensity (in a suitable unit) obtained when the excitation wavelength is changed at a particular fluorescence wavelength (for example, 550 nm).

Figure 3:
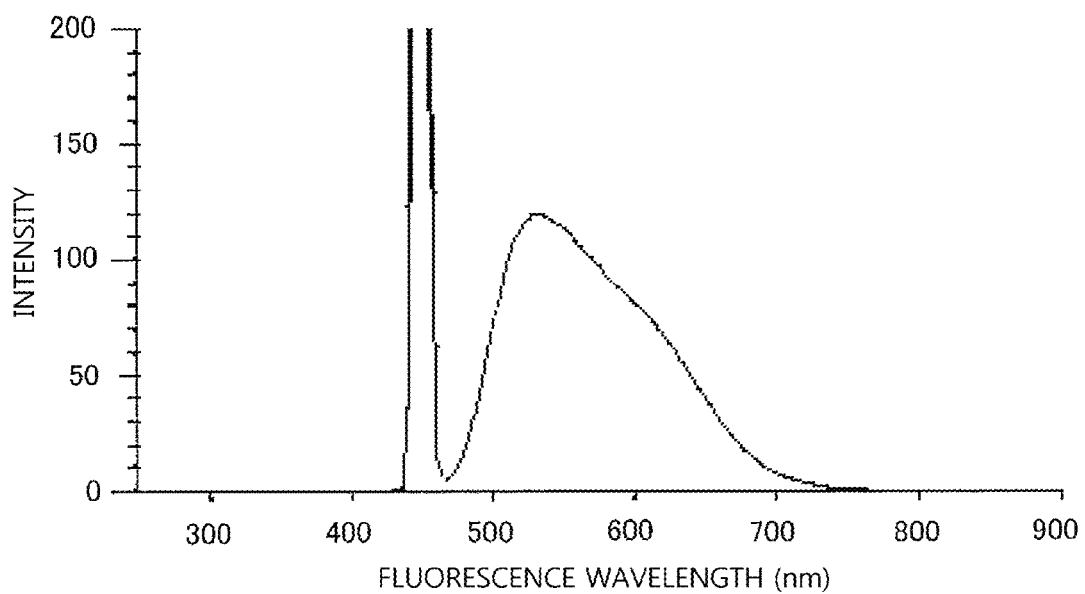
FIG. 3 is a graph for showing, in the measurement by the fluorescence spectrophotometer, a fluorescence spectrum indicating an intensity of a fluorescence wavelength.

The fluorescence spectrum shown in FIG. 3 is a spectrum obtained by measuring the fluorescence intensity for each wavelength when the sample in the sample holder 23 is irradiated with the excitation light of a fixed wavelength and the fluorescence wavelength is changed. The sample is irradiated with the excitation light from the excitation side spectroscope 12 that is set to the fixed wavelength. The fluorescent light side spectroscope 15 changes fluorescent light to be measured at the time from a measurement start wavelength to a measurement end wavelength, and a change in fluorescent light for each wavelength is detected by the detector 16 and taken in as a signal intensity by the computer 31 via the A/D converter 33. The computer 31 (controller 32) subjects the signal intensity to analysis processing to generate a spectrum that can be displayed on the display 42.

On the display 42, such a two-dimensional fluorescence spectrum of the fluorescence wavelength and the fluorescence intensity as shown in FIG. 3 is displayed as a measurement result. The spectrum of FIG. 3 indicates the fluorescence intensity obtained when the excitation light has a particular wavelength (for example, 450 nm) and the fluorescence wavelength is changed.

The time-varying spectrum shown in FIG. 4 is a spectrum obtained when the sample in the sample holder 23 is irradiated with the excitation light of a fixed wavelength to measure an intensity of fluorescent light of a fixed wavelength for each unit time. The sample is irradiated with the excitation light from the excitation side spectroscope 12 that is set to the fixed wavelength, and fluorescent light that is generated at the time is detected by the detector 16 in terms of a change in intensity of the fluorescent light for each time via the fluorescent light side spectroscope 15 that is set to the fixed wavelength at the time. The change in intensity is taken in as a signal intensity by the computer 31 via the A/D converter 33.

The display 42 displays, as a measurement result, such a two-dimensional time-varying spectrum of measurement time and the fluorescence intensity as shown in FIG. 4. The spectrum of FIG. 4 indicates a result of detecting an intensity of fluorescent light of a particular wavelength (for example, 550 nm), which corresponds to the excitation light of a particular wavelength. With the elapse of time, a change, decomposition, and the like of a fluorescent material in the sample occur, and hence the intensity is often reduced.

In FIG. 5A, a three-dimensional spectrum displayed by the display 42, in particular, a three-dimensional fluorescence spectrum, is shown. A fluorescence spectrum obtained when the excitation wavelength is fixed with respect to the sample is measured. When scanning of the fluorescence spectrum is finished, the fluorescence wavelength is reset to the measurement start wavelength, and the excitation wavelength is driven by a predetermined wavelength interval to measure a fluorescence spectrum at the next excitation wavelength. The obtained fluorescence spectra are stored in three dimensions of the excitation wavelength, the fluorescence wavelength, and the fluorescence intensity, and the process is repeated until the excitation wavelength reaches the final wavelength, with the result that the three-dimensional fluorescence spectrum can be acquired. This spectrum can be regarded as a combination of the excitation spectrum of FIG. 2 and the fluorescence spectrum of FIG. 3.

The obtained three-dimensional fluorescence spectrum is depicted in a contour map, a bird's-eye view, or other such simulated three-dimensional form by connecting the same fluorescence intensities with respective lines. The excitation wavelength and the fluorescence wavelength that form a mountain of contour lines are an excitation wavelength and a characteristic fluorescence wavelength that are suited for the sample, and the operator can easily grasp fluorescence characteristics of the excitation wavelength and the fluorescence wavelength within a measurement range of the sample. Such a three-dimensional fluorescence spectrum is useful in that a large amount of information, such as the number of components of the fluorescent material in the sample and identification of the components, can be obtained.

In FIG. 5B, another three-dimensional spectrum displayed on the display 42, in particular, a three-dimensional time-varying spectrum, is shown. A fluorescence spectrum obtained when the excitation wavelength is fixed with respect to the sample is measured. When scanning of the fluorescence spectrum is finished, the fluorescence wavelength is reset to the measurement start wavelength, and a fluorescence spectrum at the same excitation wavelength is measured after the elapse of a predetermined interval. The obtained fluorescence spectra are stored in three dimensions of the measurement time, the fluorescence wavelength, and the fluorescence intensity, and the process is repeated until the set measurement time is reached, with the result that the three-dimensional time-varying spectrum can be acquired. This spectrum can be regarded as a combination of the fluorescence spectrum of FIG. 3 and the time-varying spectrum of FIG. 4. The obtained three-dimensional time-varying spectrum is depicted in a contour map, a bird's-eye view, or other such simulated three-dimensional form by connecting the same fluorescence intensities with respective lines. Such a three-dimensional time-varying spectrum is useful in obtaining a change in time of the fluorescence spectra.

Figure 6A:
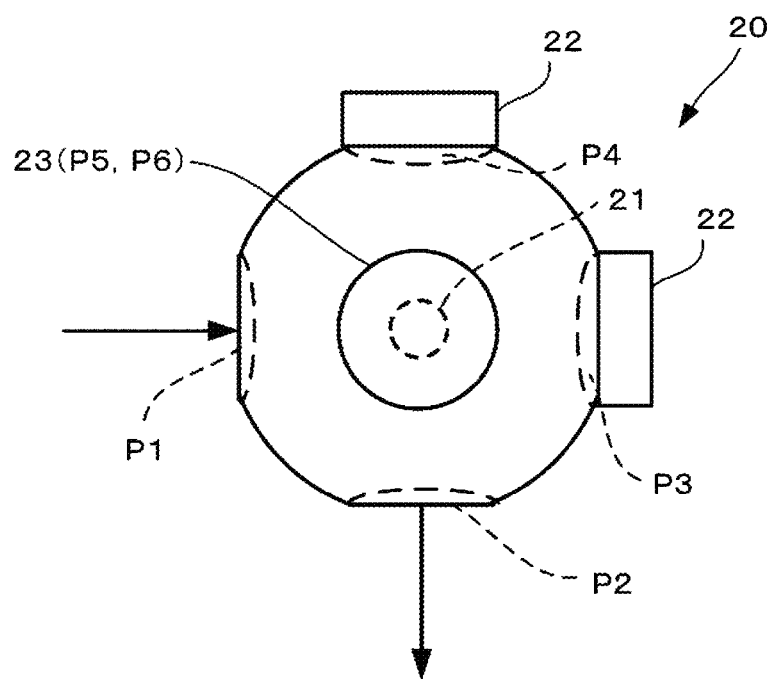
Figure 6B:
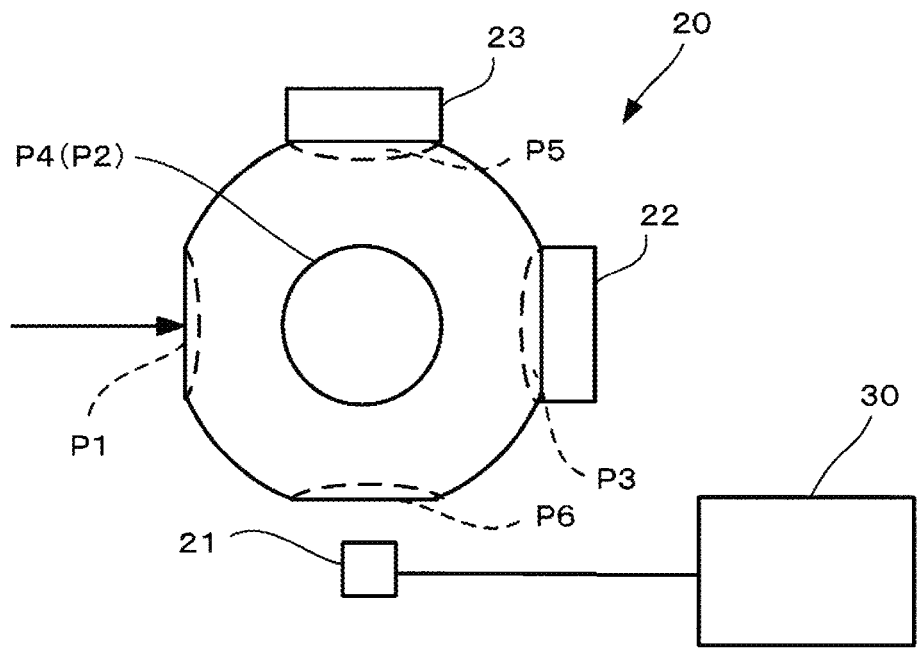

FIG. 6A and FIG. 6B are views for illustrating the details of the integrating sphere 20 in this embodiment, of which FIG. 6A is a top view of the integrating sphere 20, and FIG. 6B is a side view of the integrating sphere 20. In the integrating sphere 20 in this example, six ports (holes) P1 to P6, which pierce an outer surface and the inner surface of the integrating sphere 20, are formed. The port P1 and the port P3, the port P2 and the port P4, and the port P5 and the port P6 are formed at positions opposite to each other with a center point of the sphere being interposed therebetween. Nothing is provided on the port P1 at a position that is opposed to the beam splitter 13, and the excitation light that is generated in the excitation side spectroscope 12 and separated by the beam splitter 13 is allowed to pass through the port P1. The sample holder 23 holding the sample is mounted on the port P5. Each of the ports P3 and P4 is closed with a white plate 22, which is formed of, for example, a highly reflective white material (for example, the same material as that of the inner surface of the integrating sphere 20) to form a part of the inner surface of the integrating sphere 20. To suppress a reduction in amount of light, which is caused by the excitation light and the fluorescent light escaping through openness, the port P4, which is opposite to the port P2, is desirably, but not necessarily, closed with the white plate 22. Nothing is provided on the port P2 at a position that is opposed to the fluorescent light side spectroscope 15, and the port P6 at a position that is opposed to the camera module 21.

In this configuration, when the excitation light is allowed to enter from the port P1, the excitation light is scattered and reflected (diffusely reflected) by the inner surface of the integrating sphere 20, and the interior space of the integrating sphere 20 is filled with the excitation light. Then, there is arranged the port P2 configured to extract the fluorescent light in a direction of 90 degrees with respect to a direction of incidence of the excitation light that has entered from the port P1, and the fluorescent light emitted from the sample in the sample holder 23 passes through the port P2 to be guided to the fluorescent light side spectroscope 15, in which the spectrum is measured.

Moreover, the sample holder 23 holding the sample is placed at a position of the port P5, which is a position that is not directly irradiated with the excitation light. The camera module 21 is placed to be opposed to the port P6, which is located opposite to the port P5, that is, the sample holder 23. The camera module 21 is formed of such a lens that is focused on the sample, a stop for adjusting an amount of light, a long-pass filter configured to cut unnecessary light, an image pick-up element, and other such components. The camera module 21 is controlled by the computer 31 of the data processor 30. As long as the condition that the sample in the sample holder 23 is not directly irradiated with the excitation light is satisfied, a configuration, the number, and the like of the ports of the integrating sphere 20 are not limited to those illustrated in FIG. 6A and FIG. 6B. Moreover, diameters of the ports are all the same in this embodiment, but are not necessarily required to be the same. Moreover, it is preferred that the white plate 22 have such a size that does not allow ambient light to enter the integrating sphere from the port to which the white plate 22 is mounted. A configuration of the sample holder 23 is also not particularly limited. The material of the inner surface of the integrating sphere 20 is also not particularly limited, but is preferred to be formed of a material having a high reflectance.

Figure 7:
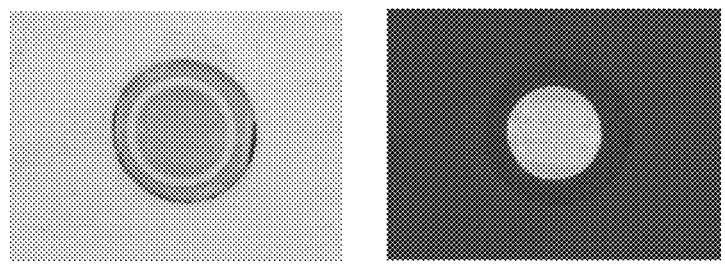
FIG. 7 is diagrams for illustrating an example of taken images.

In FIG. 7, an example of sample images (images of the sample surface) is illustrated. The sample in the sample holder 23 is irradiated with the excitation light from the light source 11 of the fluorescence spectrophotometer 1. Under a state in which the excitation side spectroscope 12 is set to zero-order light (white light), the camera module 21 can take and acquire a sample image (white light image) under a white light source. Under a state in which the excitation side spectroscope 12 is set to the monochromatic light of the target wavelength, the camera module 21 can take and acquire, as a sample image under the monochromatic light, a sample image (fluorescence image) including the fluorescent light.

In this embodiment, the sample holder 23 holding the sample is not directly irradiated with the excitation light that has entered the integrating sphere 20, and is placed at the position of the port P5, which is a position that can be irradiated with the excitation light that has been scattered by the inner surface of the integrating sphere 20. Therefore, before irradiating the sample, the excitation light that has entered from the port P1 first enters the inner surface of the integrating sphere 20 to be reflected and scattered by the inner surface, with the result that the averaged excitation light is obtained. This averaged excitation light enters the sample in the sample holder 23, and hence the unevenness of the excitation light can be reduced.

The fluorescent light is emitted from the sample that the excitation light enters, and this fluorescent light also enters the inner surface of the integrating sphere 20 to be reflected and scattered by the inner surface, and is then emitted to the outside of the integrating sphere 20 to be captured by the fluorescent light side spectroscope 15 and the detector 16. As a result, the detector 16 observes (color, brightness, and the like of) the inner surface of the integrating sphere 20 with the fluorescent light, and through the observation with the excitation light and fluorescent light with reduced unevenness, highly accurate spectra (FIG. 3 to FIG. 5B) reflecting actual conditions of the sample can be acquired.

Meanwhile, the camera module 21 is placed at the position that is opposite to (including the vicinity of the position that is opposite to) the position of the sample holder 23 when viewed from the center of the integrating sphere 20 to image the surface of the sample and the inner surface of the integrating sphere based on the fluorescent light emitted by the sample irradiated with the light from the light source 11. Therefore, the camera module 21 images the fluorescent light generated based on the excitation light with reduced unevenness, and hence can acquire highly accurate sample images (FIG. 7) reflecting the actual conditions of the sample.

Moreover, with the form of FIG. 6A and FIG. 6B, the camera module 21 is located opposite to the sample holder 23, and can directly capture the fluorescent light emitted from the surface of the sample to take the sample image, and the structure of the optical system can be prevented from becoming complicated. It should be noted, however, that the camera module 21 and the sample holder 23 are not necessarily required to be located opposite to each other.

Figure 8:
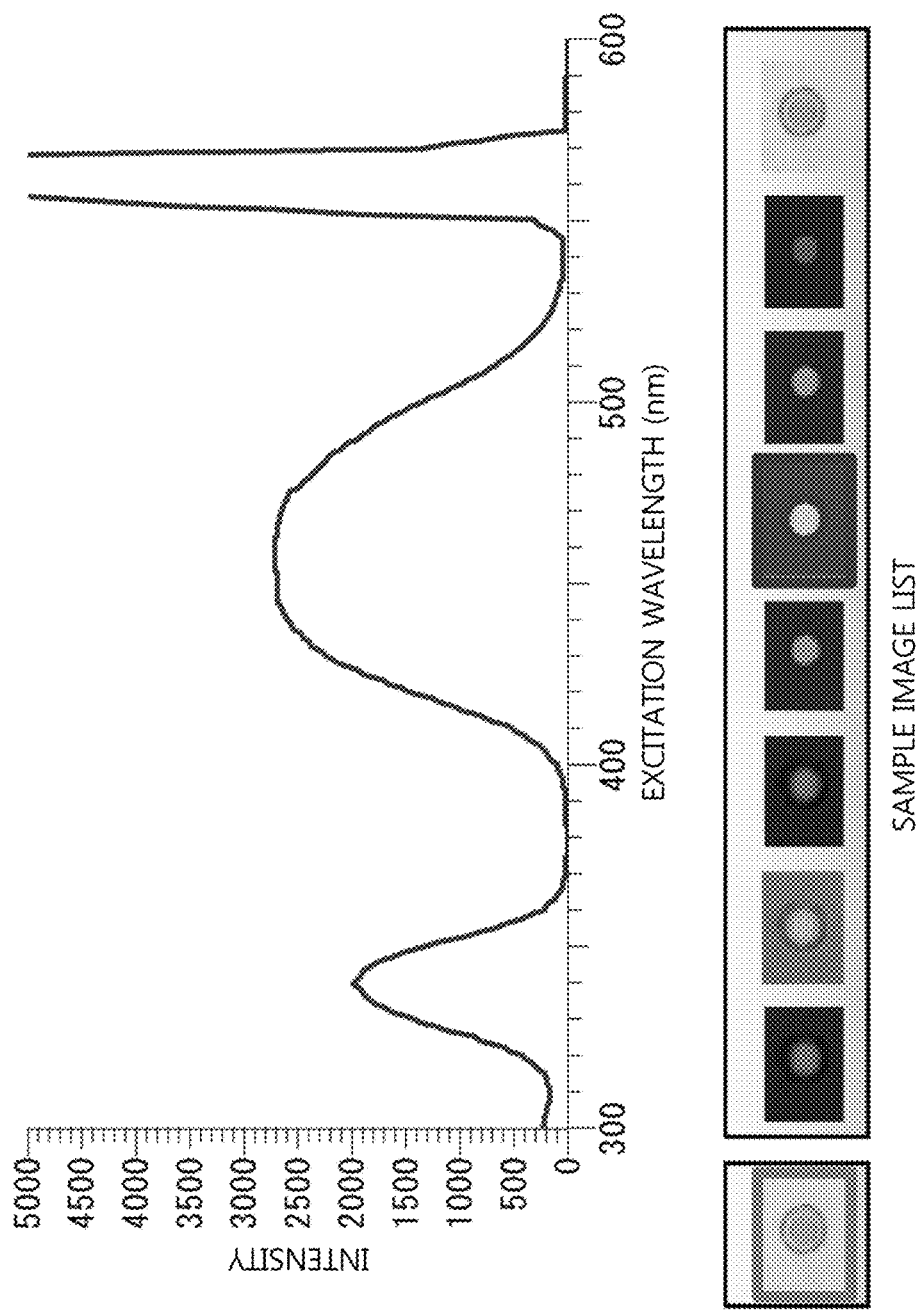
FIG. 8 is a diagram for illustrating an example of an excitation spectrum obtained when the excitation wavelength is changed, and sample images acquired in synchronization with the changes.
Figure 9:
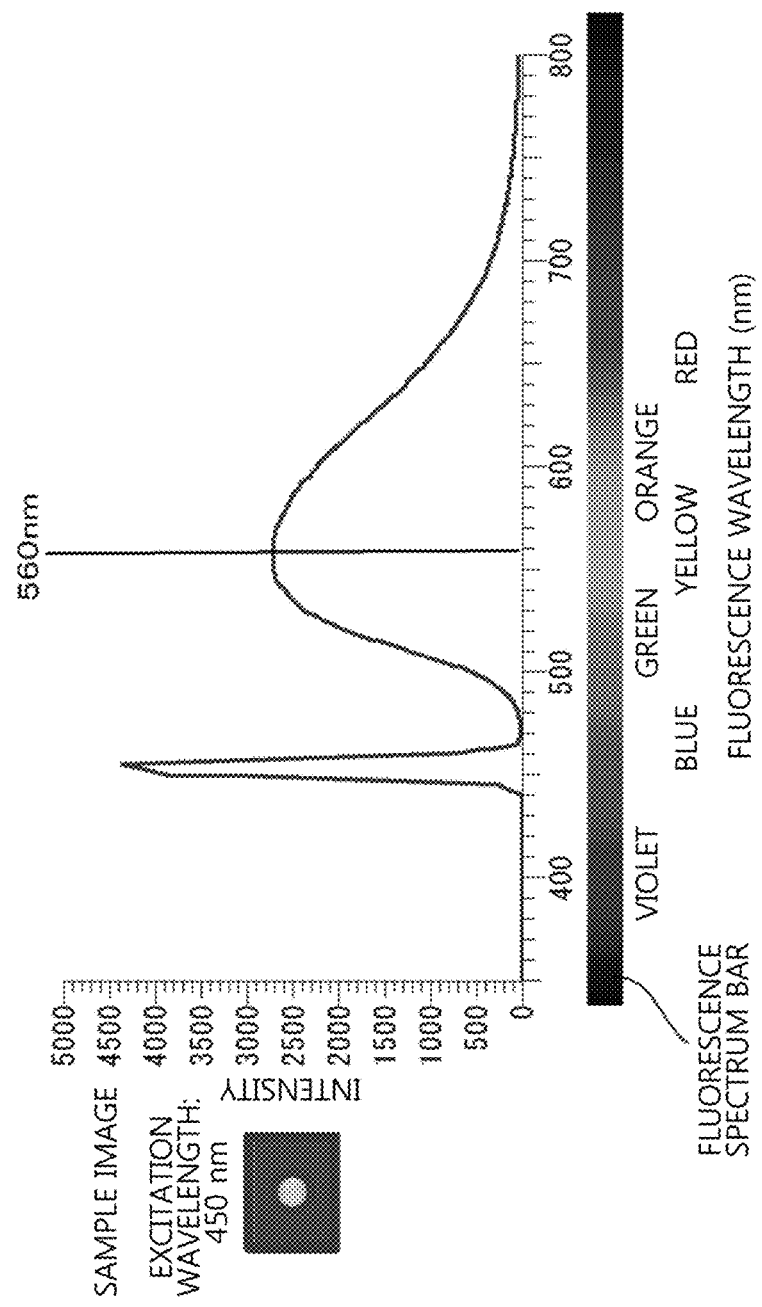
FIG. 9 is a diagram for illustrating an example of a fluorescence spectrum obtained when the excitation wavelength is fixed and the fluorescence wavelength is changed, and a sample image acquired at the excitation wavelength.
Figure 10:
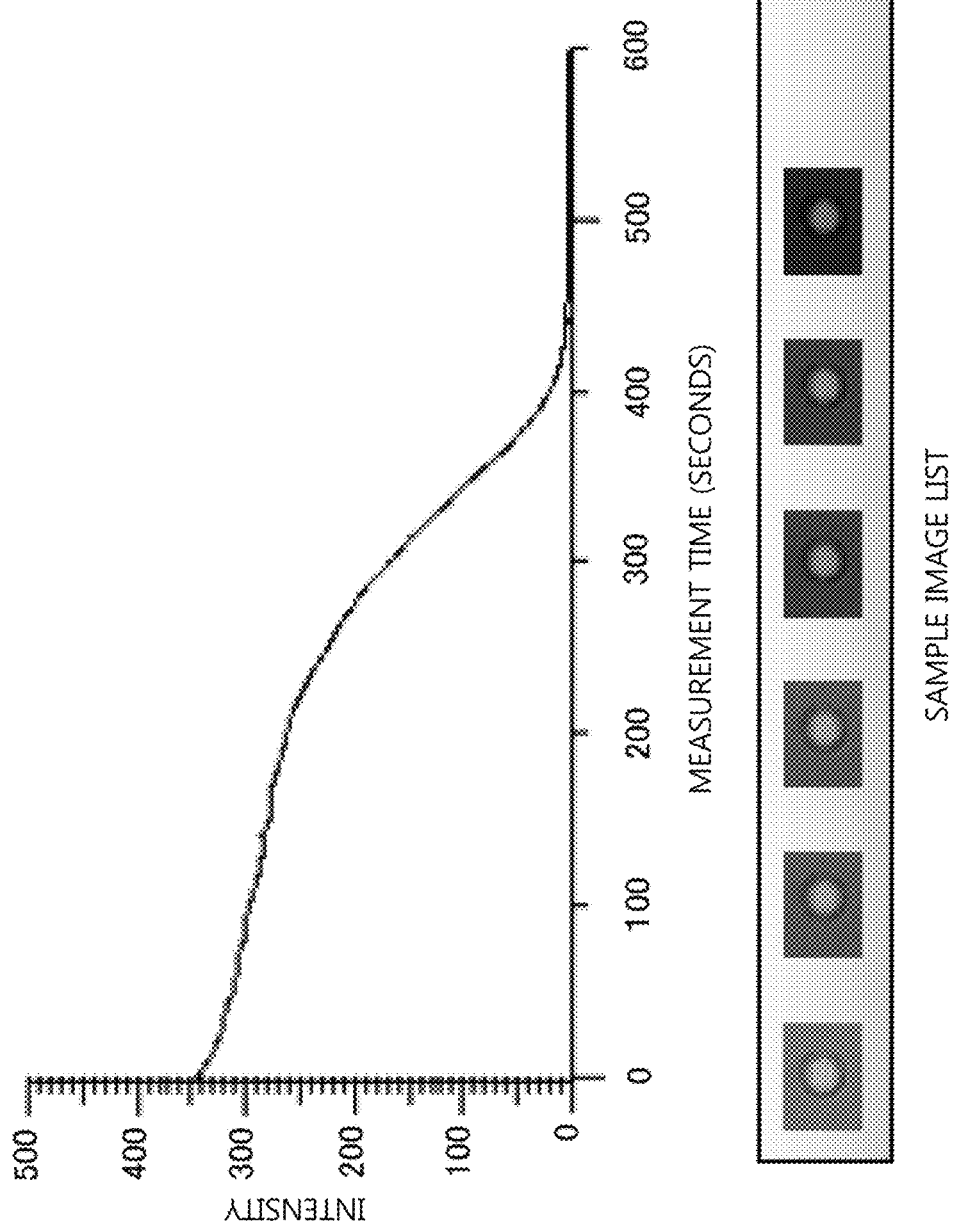
FIG. 10 is a diagram for illustrating an example of a time-varying spectrum obtained by measuring a change in time of the fluorescence intensity while fixing the excitation wavelength and the fluorescence wavelength, and sample images acquired at predetermined intervals.

As described above, the fluorescence spectrophotometer 1 according to this embodiment can acquire both excellent spectra and sample images reflecting the actual conditions of the sample, and can improve accuracy of the measurement. Moreover, the fluorescence spectrophotometer 1 according to this embodiment can increase convenience of the measurement, and further increase efficiency of the analysis. In particular, the computer 31 (controller 32) processes various kinds of measurement data (spectra, sample image, and the like) obtained by the photometer 10, and the display 42 displays, based on the processed measurement data, the various spectra acquired by the detector 16, and the sample images acquired by the camera module 21 in an arrangement in the same screen. As a result, the convenience of the measurement and the efficiency of the analysis can be further increased. Such examples are described below. In FIG. 8 to FIG. 10, there are illustrated examples of a screen display in which a two-dimensional spectrum including two axes, which can also be obtained by the fluorescence spectrophotometer 1 according to this embodiment, and the sample images are displayed in an arrangement.

In FIG. 8, there is illustrated an example in which an excitation spectrum obtained when the excitation wavelength of the fluorescence spectrophotometer 1 is changed, and sample images acquired by the camera module 21 in synchronization with the change are displayed in an arrangement. In the excitation spectrum, the horizontal axis indicates the wavelength of the excitation light with which the sample is irradiated, and the vertical axis indicates a fluorescence intensity at a particular fluorescence wavelength. Depending on the wavelength of the excitation light with which the sample is irradiated, the camera module 21 images the sample at particular (constant) wavelength intervals. The computer 31 (controller 32) generates a sample image list including a plurality of sample images with each sample image being associated with an excitation wavelength, and the display 42 displays the sample image list in the arrangement so that the sample image list corresponds to the excitation wavelength axis of the excitation spectrum. The white light image may be displayed at an appropriate place, for example, to the left of the sample image list. With this configuration, the operator can observe the excitation spectrum and the sample image list in comparison with each other, and can easily grasp the state of the sample at each excitation wavelength. The sample images reflecting the excitation spectrum are obtained such that when the fluorescence intensity in the excitation spectrum is high, the taken sample image is also in a state of emitting bright light, and when the fluorescence intensity is low on the contrary, the sample image is also dark. Meanwhile, the excitation spectrum observes the intensity at the fixed fluorescence wavelength, and hence information on intensities at the other fluorescence wavelengths cannot be obtained. However, through acquisition of the sample images at different excitation wavelengths, a change in hue of the sample, a fluorescence distribution in the sample, and the like can be grasped.

In FIG. 9, there is illustrated an example of a fluorescence spectrum obtained when the excitation wavelength of the fluorescence spectrophotometer 1 is fixed and the fluorescence wavelength is changed, and a sample image acquired by the camera module 21 at the excitation wavelength. The computer 31 (controller 32) identifies the sample image at the excitation wavelength, and the display 42 displays the fluorescence spectrum and the sample image in an arrangement. In the fluorescence spectrum, the horizontal axis indicates a wavelength of the fluorescent light emitted by the sample, and the vertical axis indicates an intensity of the fluorescent light. The fluorescence spectrum has correlation with emission color of the sample image but is average information, and is useful information in identifying the hue of the sample and an emission distribution in the sample in the sample image. Moreover, a fluorescence spectrum bar indicating a color corresponding to the fluorescence wavelength is also displayed.

In FIG. 10, there is illustrated an example of a time-varying spectrum for measuring a change in time of the fluorescence intensity while fixing the excitation wavelength and the fluorescence wavelength of the fluorescence spectrophotometer 1, and sample images acquired at predetermined (constant) time intervals. In the time-varying spectrum, the horizontal axis indicates the time, and the vertical axis indicates the fluorescence intensity. After the irradiation of the sample with the excitation light is started, the camera module 21 images the sample at the predetermined (constant) time intervals. The computer 31 (controller 32) generates a sample image list including a plurality of sample images with each sample image being associated with an excitation wavelength, and the display 42 displays the sample image list in an arrangement so that the sample image list corresponds to the measurement time axis of the time-varying spectrum. With this configuration, the operator can observe the time-varying spectrum and the sample image list in comparison with each other, and can easily grasp the state of the sample at each measurement time.

Figure 11:
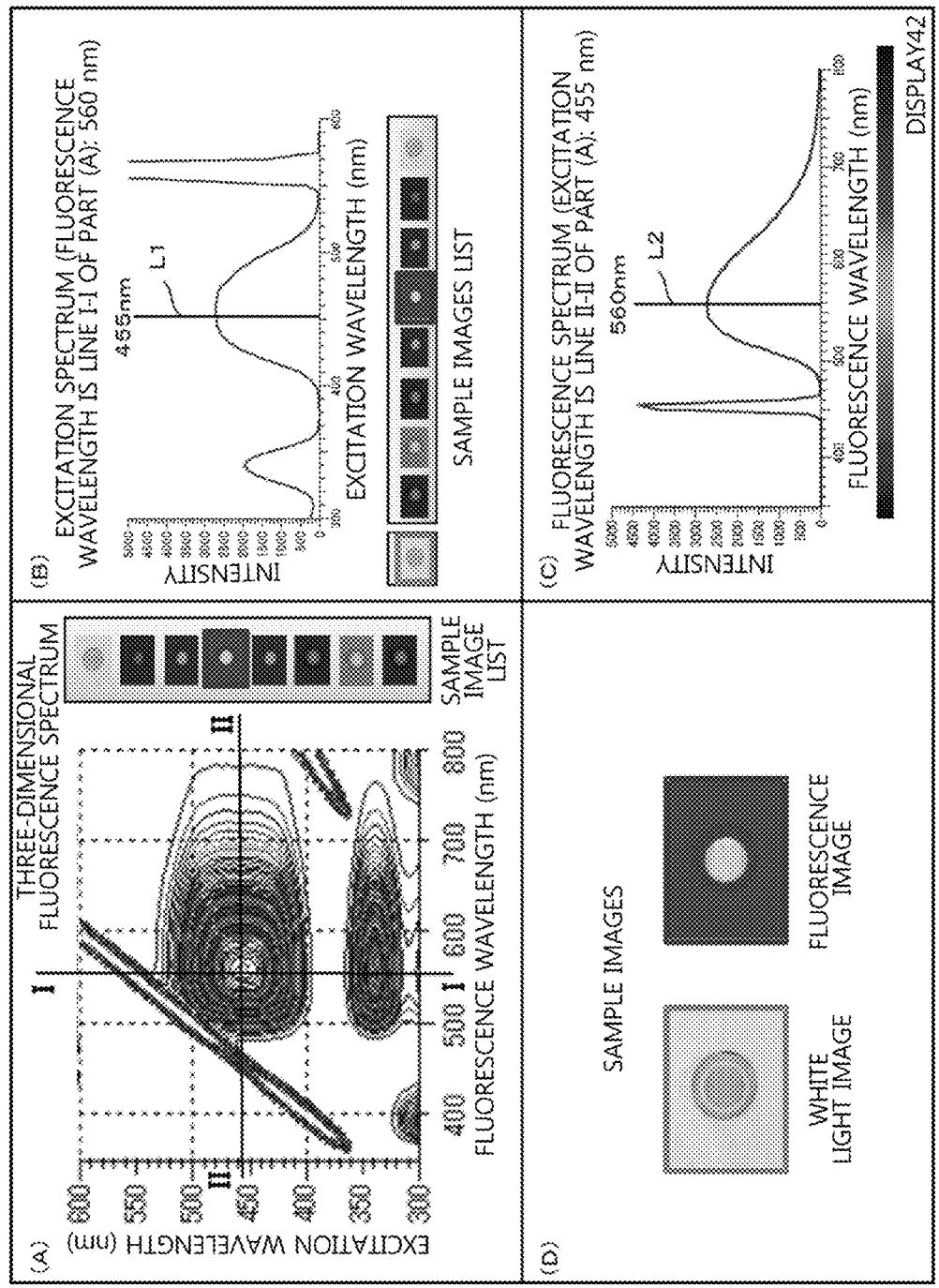
FIG. 11 is a diagram for illustrating an example of integrated data display by a display.

In FIG. 11, there is illustrated an example in which, based on measurement data at least containing the various spectra and the sample images obtained by the photometer 10, which has been processed by the computer 31 (controller 32), the display 42 displays the spectra, the sample images, and other such information in the same screen after the measurement is finished. With the display 42 providing measurement data display (integrated data display) of an integrated form, in which such various kinds of data are integrated, the operator can collectively grasp the various kinds of data, and can easily grasp properties of the sample.

When the operator provides, from the operation panel 41, input to the effect that the integrated data display is to be displayed, the computer 31 (controller 32) outputs an instruction corresponding to the input to the display 42. Receiving the output, the display 42 displays 1) a three-dimensional fluorescence spectrum in an upper left region (A) of a screen (hereinafter referred to as "Part (A) of FIG. 11"), 2) an excitation spectrum taken from the three-dimensional fluorescence spectrum in an upper right region (B) of the screen (hereinafter referred to as "Part (B) of FIG. 11"), 3) a fluorescence spectrum taken from the three-dimensional fluorescence spectrum in a lower right region (C) of the screen (hereinafter referred to as "Part (C) of FIGS. 11"), and 4) sample images in a lower left region (D) of the screen (hereinafter referred to as "Part (D) of FIG. 11") respectively in forms of sub-screens. It should be noted, however, that which sub-screen is to be displayed in which region may be freely selected, and is not particularly limited. Moreover, in this embodiment, the number of regions (the number of division of the screen or the number of sub-screens) is four, but the number is not particularly limited. The form of division is also not particularly limited. The following description is given based on the arrangement of FIG. 11.

The three-dimensional fluorescence spectrum illustrated in Part (A) of FIG. 11 can be obtained similarly to that of FIG. 5A. In other words, a fluorescence spectrum obtained when the excitation wavelength is fixed with respect to the sample is measured. Then, when the scanning of the fluorescence spectrum is finished, the fluorescence wavelength is reset to the measurement start wavelength, and the excitation wavelength is driven by the predetermined wavelength interval to measure a fluorescence spectrum at the next excitation wavelength. The obtained fluorescence spectra are stored in the three dimensions of the excitation wavelength, the fluorescence wavelength, and the fluorescence intensity, and the process is repeated until the excitation wavelength reaches the final wavelength, with the result that the three-dimensional fluorescence spectrum can be acquired.

At this time, the excitation wavelength is driven at intervals of from about 5 nm to about 10 nm to acquire the three-dimensional fluorescence spectrum. The camera module 21 takes the sample images in synchronization with the excitation wavelength intervals. The computer 31 (controller 32) generates the sample image list including a plurality of sample images corresponding to the excitation wavelengths. Then, as illustrated in Part (A) of FIG. 11, with the display 42 displaying the sample image list so that the sample image list corresponds to the excitation wavelength axis (vertical axis) corresponding to the excitation wavelength, the operator can check three-dimensional fluorescence spectrum characteristics and the sample image at each excitation wavelength in comparison with each other. At this time, in FIG. 11, the sample image list taken to correspond to the excitation wavelength is displayed to the right of the three-dimensional fluorescence spectrum. However, it is only preferred that the sample image list be displayed in comparison to the excitation wavelength, and the sample image list may be displayed to the left of the three-dimensional fluorescence spectrum.

In Part (B) of FIG. 11, the excitation spectrum taken along the line I-I in Part (A) of FIG. 11 is displayed. The line I-I of the vertical axis generated by the computer 31 (controller 32) and displayed by the display 42 is a selection tool with which a particular fluorescence wavelength corresponding to a particular position along the fluorescence wavelength axis (horizontal axis) of the three-dimensional fluorescence spectrum can be selected. With the operator operating with the use of the operation panel 41, the line I-I can be moved (slid) in a left-and-right direction (horizontal direction) to select any fluorescence wavelength corresponding to a stop position. The line I-I is, so to speak, a selection line for selecting the fluorescence wavelength, and is sometimes called "trace bar", for example.

A cross section of the three-dimensional fluorescence spectrum in Part (A) of FIG. 11 at the position at which the line I-I is stopped corresponds to the excitation spectrum in Part (B) of FIG. 11. Therefore, with the operator shifting the line I-I in Part (A) of FIG. 11 to the left or right through the operation of the operation panel 41 to change the fluorescence wavelength, the excitation spectrum in Part (B) of FIG. 11 is changed in synchronization. In this example, the line I-I in Part (A) of FIG. 11 is selecting the fluorescence wavelength of 560 nm, and the excitation spectrum for the fluorescence wavelength of 560 nm is displayed in Part (B) of FIG. 11. Moreover, the sample images are acquired in synchronization with the excitation wavelength, and hence it is preferred that the sample image list be displayed below the excitation wavelength axis.

In Part (C) of FIG. 11, the fluorescence spectrum taken along the line II-II in Part (A) of FIG. 11 is displayed. The line II-II of the horizontal axis generated by the computer 31 (controller 32) and displayed by the display 42 is a selection tool with which a particular excitation wavelength corresponding to a particular position along the excitation wavelength axis (vertical axis) of the three-dimensional fluorescence spectrum can be selected. With the operator operating with the use of the operation panel 41, the line II-II can be moved (slid) in an up-and-down direction (vertical direction) to select any excitation wavelength corresponding to a stop position. The line II-II is, so to speak, a selection line for selecting the excitation wavelength, and is sometimes called "trace bar", for example.

A cross section of the three-dimensional fluorescence spectrum in Part (A) of FIG. 11 at the position at which the line II-II is stopped corresponds to the fluorescence spectrum in Part (C) of FIG. 11. Therefore, with the operator shifting the line II-II in Part (A) of FIG. 11 upward or downward through the operation of the operation panel 41 to change the excitation wavelength, the fluorescence spectrum in Part (C) of FIG. 11 is changed in synchronization. In this example, the line II-II in Part (A) of FIG. 11 is selecting the excitation wavelength of 455 nm, and the fluorescence spectrum for the excitation wavelength of 455 nm is displayed in Part (C) of FIG. 11. Moreover, a fluorescence spectrum bar indicating a color corresponding to the fluorescence wavelength is also displayed.

In Part (D) of FIG. 11, the sample images are displayed. In this example, a white light image is displayed on the left, and a fluorescence image is displayed on the right. The white light image is always constant. The fluorescence image corresponds to a fluorescence image at the fluorescence wavelength and the excitation wavelength selected by the line I-I and the line II-II in Part (A) of FIG. 11, respectively, and in this example, a fluorescence image at the excitation wavelength of 455 nm and the fluorescence wavelength of 560 nm is displayed.

In this example, in Part (B) of FIG. 11, an excitation wavelength selection line (bar) L1 indicating the excitation wavelength (455 nm) that is being selected by the line II-II is displayed. Moreover, in Part (C) of FIG. 11, a fluorescence wavelength selection line (bar) L2 indicating the fluorescence wavelength (560 nm) that is being selected by the line I-I is displayed. Those selection lines L1 and L2 easily indicate which wavelength is selected for a sample image in each of the excitation spectrum and the fluorescence spectrum to display the sample image in Part (D) of FIG. 11. It is desired that, with movements of the line I-I and the line II-II, the selection lines L1 and L2 be also moved in synchronization. Moreover, through selection of any one of the sample images in the sample image lists in Part (A) of FIG. 11 and Part (B) of FIG. 11, spectra corresponding to the selection may be displayed in Parts (A) to (C) of FIG. 11, and a fluorescence image that is enlarged to correspond to the selection may be displayed in Part (D) of FIG. 11.

Figure 12:
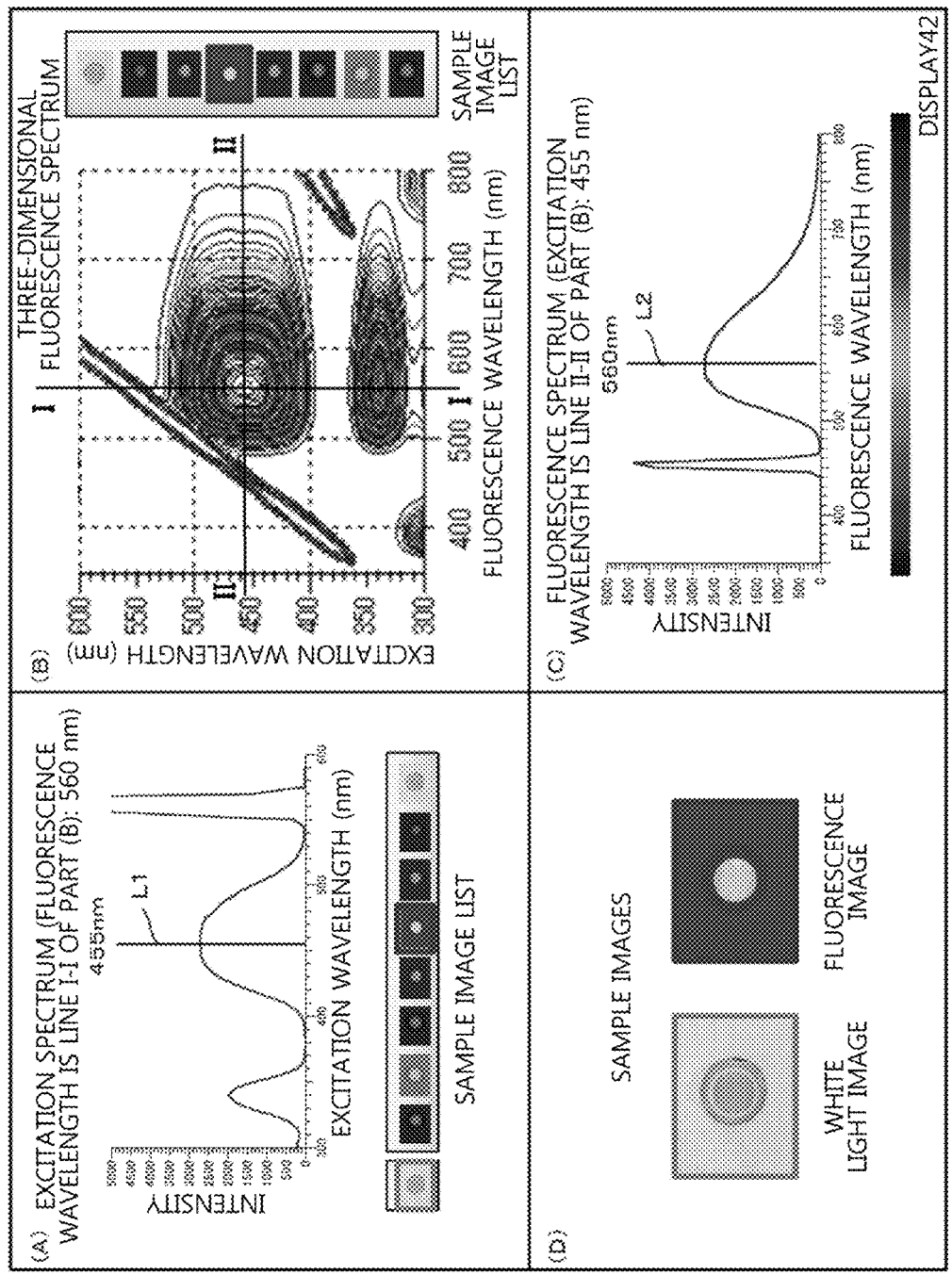
FIG. 12 is a diagram for illustrating a modification example of the display of FIG. 11.

As in FIG. 12, the three-dimensional fluorescence spectrum may be arranged in Part (B) of FIG. 12, the excitation spectrum may be taken in Part (A) of FIG. 12, the fluorescence spectrum may be taken in Part (C) of FIG. 12, and the sample images may be displayed at the position of Part (D) of FIG. 12. With this arrangement, it becomes easier to grasp correspondence of the vertical axis (excitation wavelength axis) and the horizontal axis (fluorescence wavelength axis) displayed in the three-dimensional fluorescence spectrum to the excitation spectrum and the fluorescence spectrum taken from the three-dimensional fluorescence spectrum. There are cases in which the three-dimensional fluorescence spectrum may be displayed with the excitation wavelength being indicated by the horizontal axis and the fluorescence wavelength being indicated by the vertical axis, and in such cases, positions of the taken excitation spectrum and fluorescence spectrum may be inverted.

Figure 13:
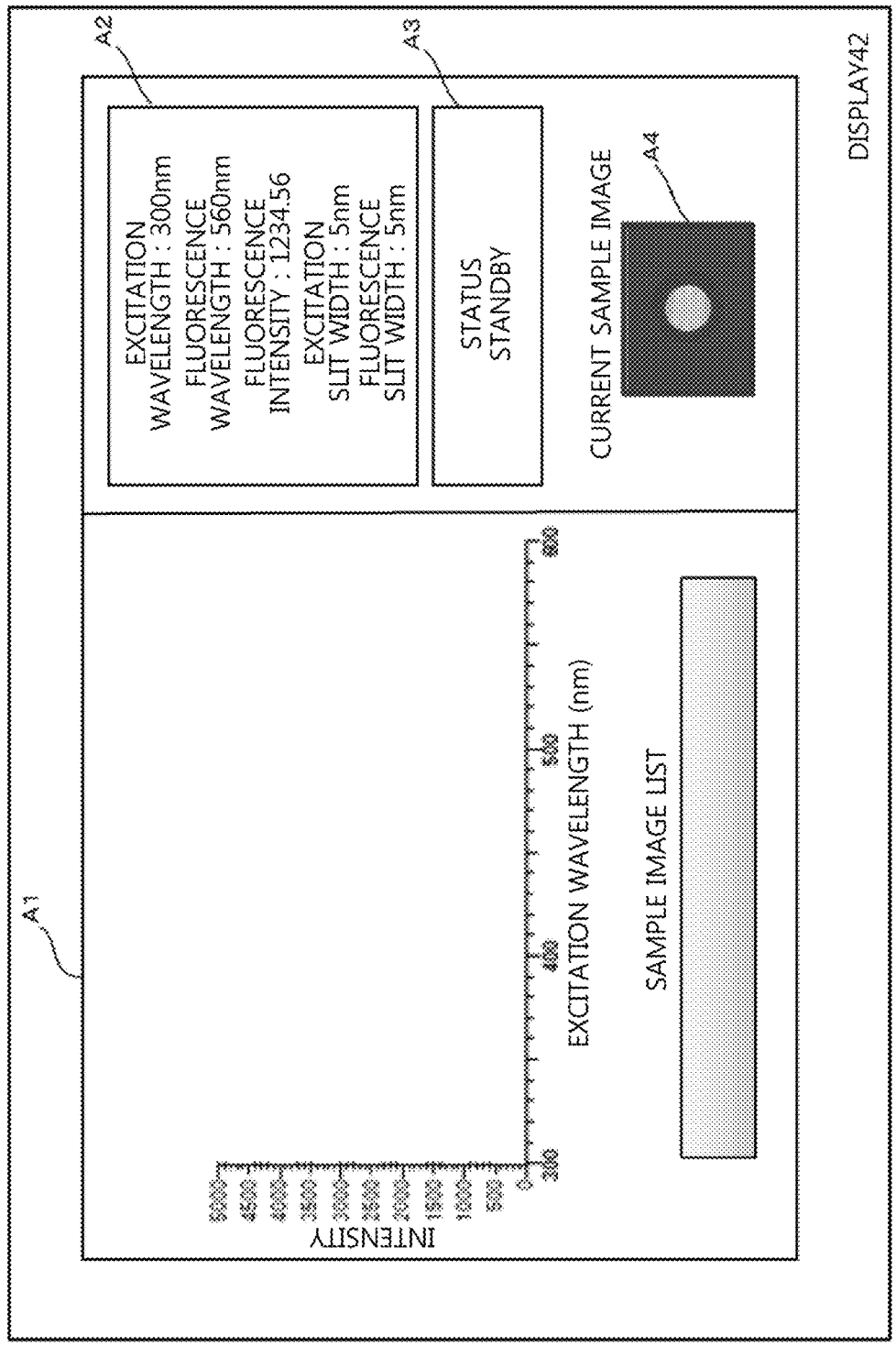
FIG. 13 is a diagram for illustrating an example of a measurement screen during standby.

In FIG. 13, there is illustrated, of the various spectra and other such data described above, an example of a measurement screen during standby immediately before the measurement for acquiring the excitation spectrum. When the operator operates the operation panel 41 to perform a predetermined measurement standby operation, the display 42 displays, as the measurement screen, a measurement display area A1, a measurement condition display area A2, a status display area A3, and a sample image display area A4. In the measurement display area A1, the spectrum and the sample image list based on the acquired data of the sample are displayed. In the measurement condition display area A2, the measurement conditions input by the operator with the use of the operation panel 41 are displayed. The measurement conditions include the excitation wavelength, the fluorescence wavelength, the fluorescence intensity, an excitation slit width, a fluorescence slit width, and other such conditions. In the status display area A3, a status corresponding to the current operating state of the fluorescence spectrophotometer 1 is displayed. In the sample image display area A4, the latest updated sample image is displayed. During standby, no data is obtained for the sample, and hence nothing is displayed in the measurement display area A1.

Figure 14:
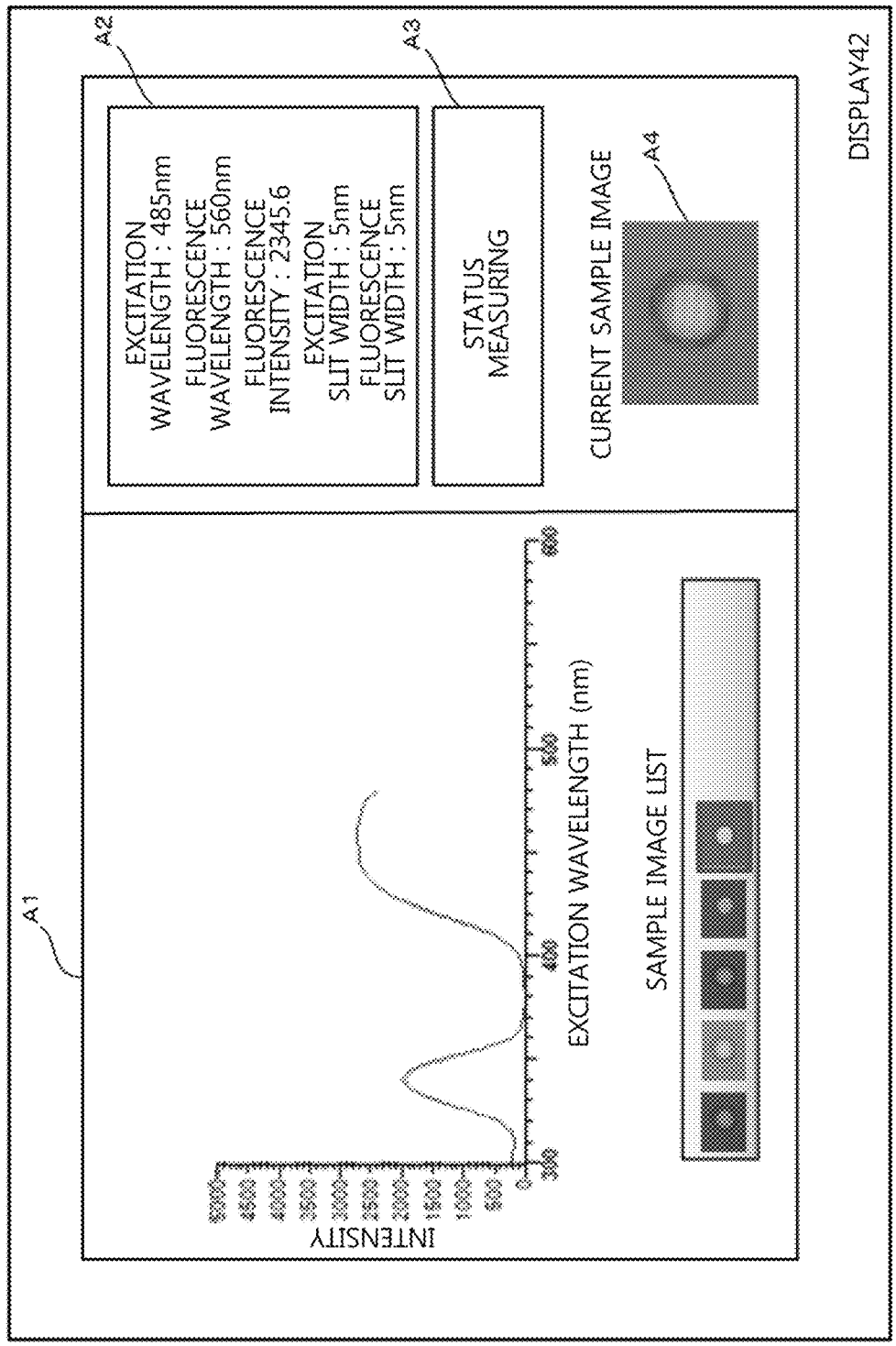
FIG. 14 is a diagram for illustrating an example of the measurement screen during measurement of the excitation spectrum.

In FIG. 14, there is illustrated an example of the measurement screen during measurement of the excitation spectrum. When the operator operates the operation panel 41 to perform a predetermined measurement start operation, the fluorescence spectrophotometer 1 starts the measurement, and the display 42 starts displaying the excitation spectrum in the measurement display area A1. At the same time, the camera module 21 acquires the sample images at the constant excitation wavelength intervals, and the sample image list is displayed at a position corresponding to the excitation wavelength axis of the excitation spectrum. The operator has input a photography interval per excitation wavelength of the sample image, which is a measurement condition, in advance with the use of the operation panel 41. When the measurement is complete, the excitation spectrum and the sample image list corresponding to the excitation wavelength are displayed as illustrated in FIG. 8.

In the same manner as illustrated in FIG. 13 and FIG. 14, the fluorescence spectrum illustrated in FIG. 9 can be acquired.

Figure 15:
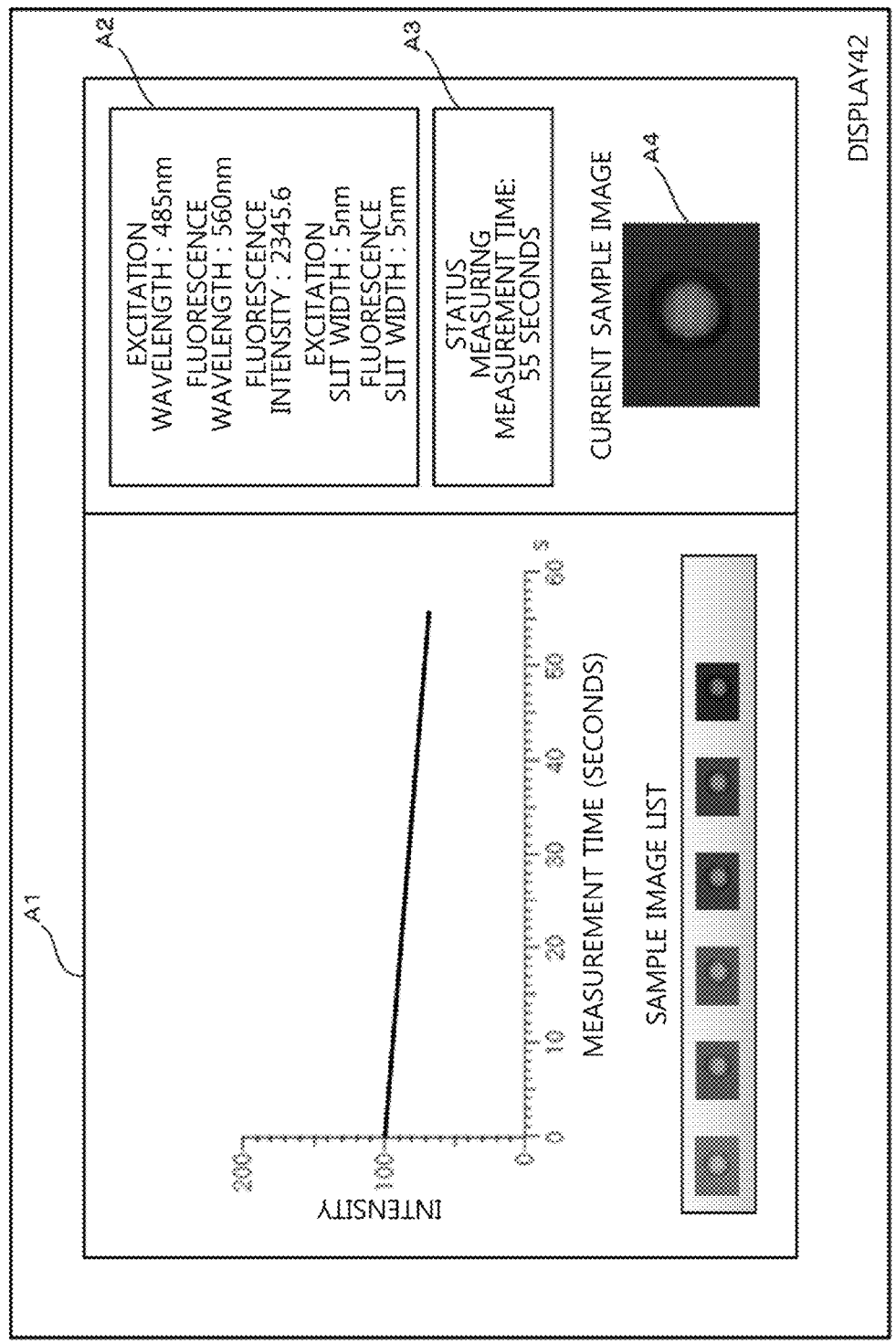
FIG. 15 is a diagram for illustrating an example of the measurement screen during measurement of the change in time.

In FIG. 15, there is illustrated an example of the measurement screen during measurement of the change in time. When the measurement is started, the display 42 displays the change in time of the fluorescence intensity in the measurement display area A1. At the same time, the sample images are acquired at the constant time intervals, and the sample image list is displayed at a position corresponding to the time axis of the change in time. The operator has input a photography interval per time of the sample images, which is a measurement condition, in advance with the use of the operation panel 41. When the measurement is complete, the change in time of the fluorescence intensity and the sample image list corresponding to the time are displayed as illustrated in FIG. 10.

Figure 16:
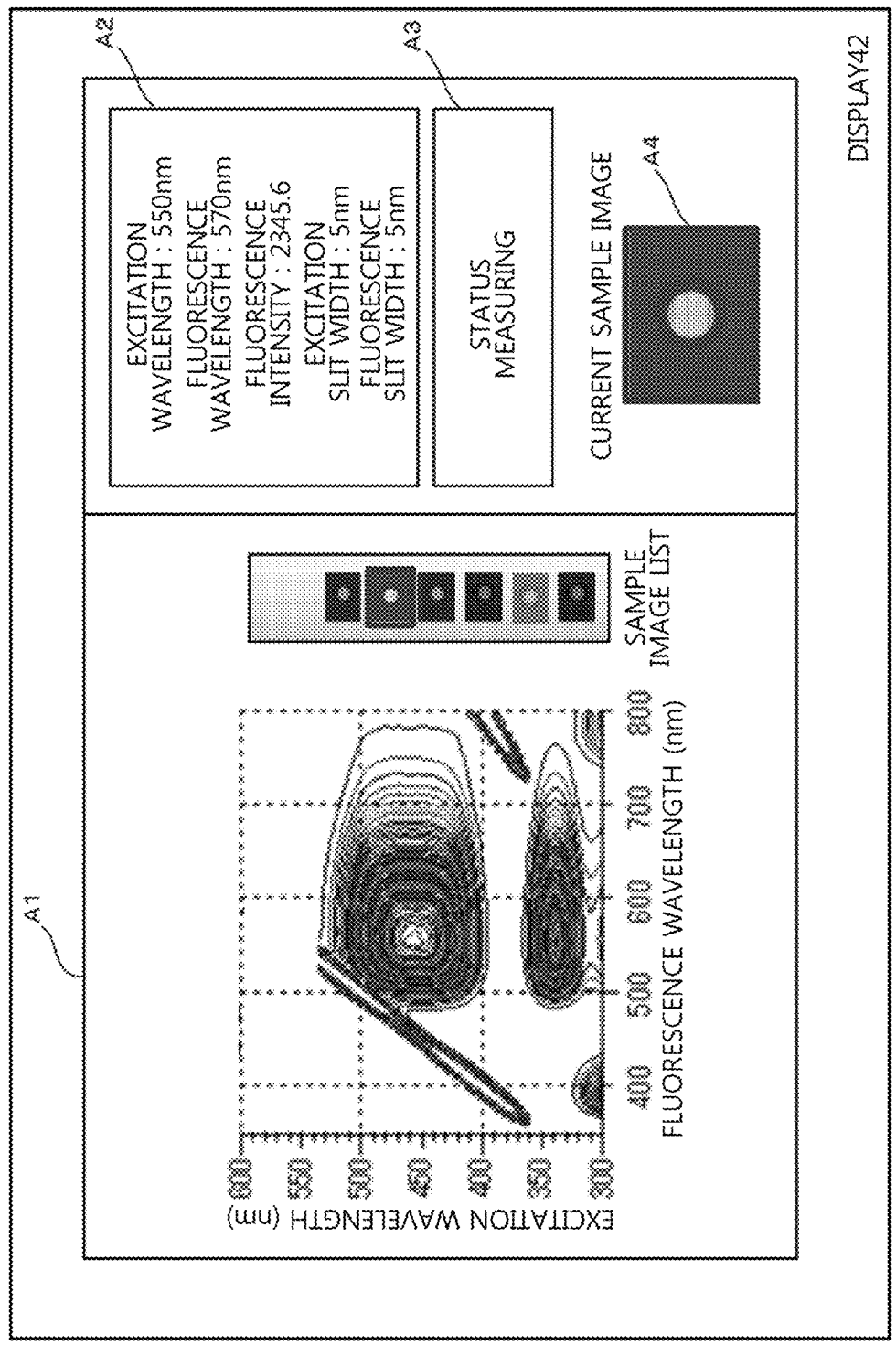
FIG. 16 is a diagram for illustrating an example of the measurement screen during measurement of the three-dimensional fluorescence spectrum.

In FIG. 16, there is illustrated an example of the measurement screen during measurement of the three-dimensional fluorescence spectrum. When the measurement is started, the display 42 displays the three-dimensional fluorescence spectrum in the measurement display area A1. At the same time, the sample images are acquired at the constant excitation wavelength intervals, and the sample image list is displayed at a position corresponding to the excitation wavelength axis of the three-dimensional fluorescence spectrum. The operator has input a photography interval per excitation wavelength of the sample images, which is a measurement condition, in advance with the use of the operation panel 41.

Of the operations described above, after the data illustrated in FIG. 8, FIG. 9, and FIG. 16 is acquired, the operator operates the operation panel 41 to perform an operation to the effect that predetermined integrated data display is to be generated. Then, the computer 31 (controller 32) processes those pieces of data, and outputs an output instruction to the display 42. In response, the display 42 performs the integrated data display illustrated in FIG. 11.

Moreover, of the operations described above, after the data illustrated in FIG. 9, FIG. 10, and FIG. 5B is acquired, the operator operates the operation panel 41 to perform an operation to the effect that predetermined integrated data display is to be generated. Then, the computer 31 (controller 32) processes those pieces of data, and outputs an output instruction to the display 42. In response, the display 42 performs the integrated data display illustrated in FIG. 17.

Figure 17:
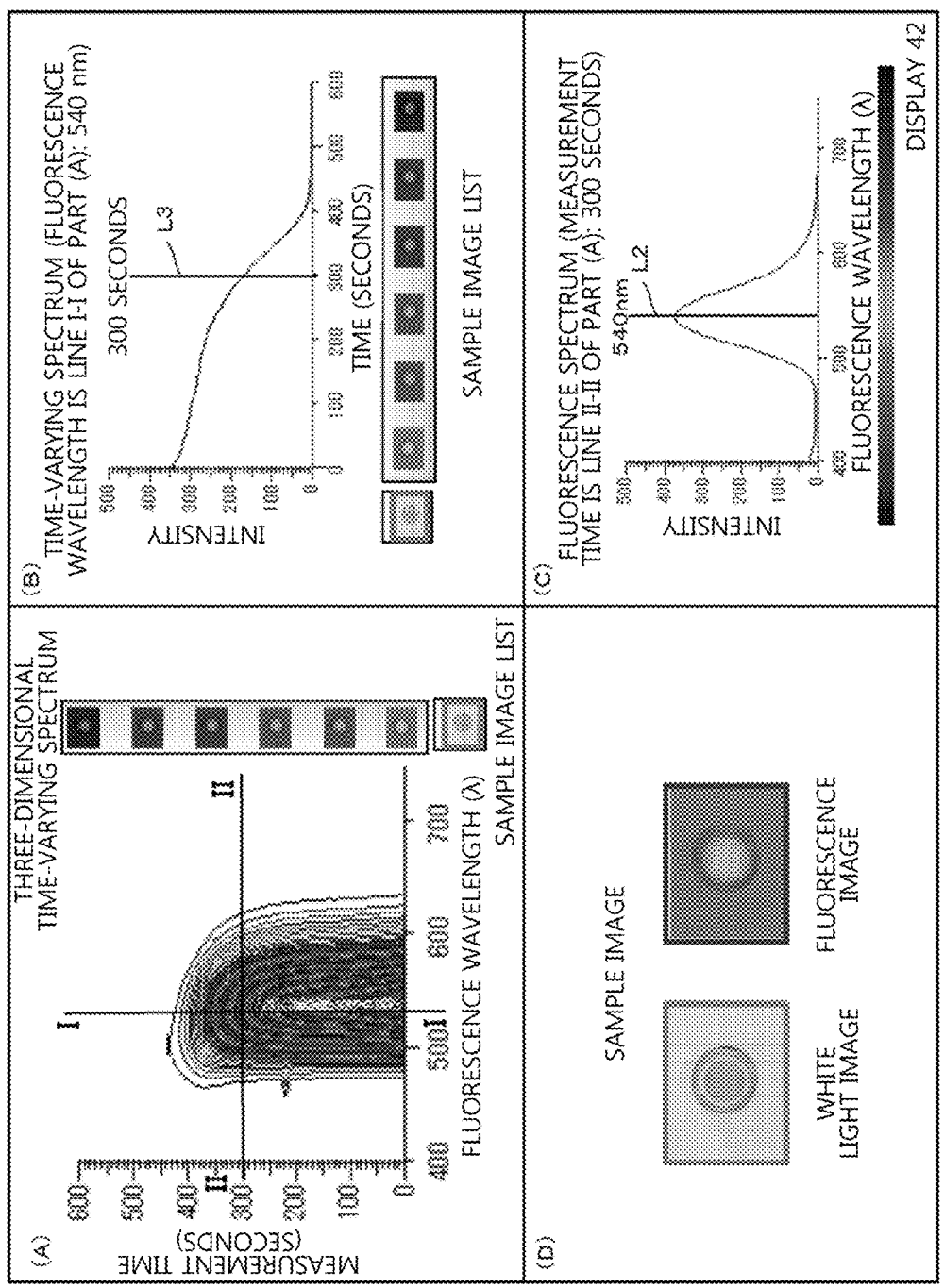
FIG. 17 is a diagram for illustrating an example of integrated data display that is different from FIG. 11.

FIG. 17 is considered as another version of the example of FIG. 11, and there is illustrated an example in which, based on the measurement data at least containing the various spectra and the sample images obtained by the photometer 10, which has been processed by the computer 31 (controller 32), the display 42 displays the spectra, the sample images, and other such information in the same screen after the measurement is finished. With the display 42 providing measurement data display (integrated data display) of an integrated form, in which such various kinds of data are integrated, the operator can collectively grasp the various kinds of data, and can easily grasp the properties of the sample.

When the operator provides, from the operation panel 41, input to the effect that the integrated data display is to be displayed, the computer 31 (controller 32) outputs an instruction corresponding to the input to the display 42. Receiving the output, the display 42 displays 1) a three-dimensional time-varying spectrum in an upper left region (A) of a screen (hereinafter referred to as "Part (A) of FIG. 17"), 2) a time-varying spectrum taken from the three-dimensional time-varying spectrum in an upper right region (B) of the screen (hereinafter referred to as "Part (B) of FIG. 17"), 3) a fluorescence spectrum taken from the three-dimensional time-varying spectrum in a lower right region (C) of the screen (hereinafter referred to as "Part (C) of FIGS. 17"), and 4) sample images in a lower left region (D) of the screen (hereinafter referred to as "Part (D) of FIG. 17") respectively in forms of sub-screens. It should be noted, however, that which sub-screen is to be displayed in which region may be freely selected, and is not particularly limited. Moreover, in this embodiment, the number of regions (the number of division of the screen or the number of sub-screens) is four, but the number is not particularly limited. The form of division is also not particularly limited. The following description is given based on the arrangement of FIG. 17.

The three-dimensional time-varying spectrum illustrated in Part (A) of FIG. 17 can be obtained similarly to that of FIG. 5B. In other words, a fluorescence spectrum obtained when the excitation wavelength is fixed with respect to the sample is measured. Then, when the scanning of the fluorescence spectrum is finished, the fluorescence wavelength is reset to the measurement start wavelength, and a fluorescence spectrum is measured after the elapse of the predetermined interval. The obtained fluorescence spectra are stored in the three dimensions of the measurement time, the fluorescence wavelength, and the fluorescence intensity, and the process is repeated until the set measurement time is reached, with the result that the three-dimensional time-varying spectrum is acquired. At this time, the measurement time is driven at intervals of from about 5 seconds to about 10 seconds to acquire the three-dimensional time-varying spectrum.

The camera module 21 takes the sample images in synchronization with the measurement time intervals. The computer (controller 32) generates the sample image list including a plurality of sample images corresponding to the measurement times. Then, as illustrated in Part (A) of FIG. 17, with the display 42 displaying the sample image list so that the sample image list corresponds to the measurement time axis (vertical axis) corresponding to the measurement time, the operator can check three-dimensional time-varying spectrum characteristics and the sample image at each measurement time in comparison with each other. At this time, in FIG. 17, the sample image list taken to correspond to the measurement time is displayed to the right of the three-dimensional time-varying spectrum. However, it is only preferred that the sample image list be displayed in comparison to the measurement time, and hence the sample image list may be displayed to the left of the three-dimensional time-varying spectrum.

In Part (B) of FIG. 17, the time-varying spectrum taken along the line I-I in Part (A) of FIG. 17 is displayed. The line I-I of the vertical axis generated by the computer 31 (controller 32) and displayed by the display 42 is a selection tool for selecting a particular fluorescence wavelength corresponding to a particular position along the horizontal axis of the three-dimensional time-varying spectrum. With the operator operating with the use of the operation panel 41, the line I-I can be moved (slid) in the left-and-right direction (horizontal direction) to select any fluorescence wavelength corresponding to a stop position. The line I-I is, so to speak, a selection line for selecting the fluorescence wavelength, and is sometimes called "trace bar", for example.

A cross section of the three-dimensional time-varying spectrum in Part (A) of FIG. 17 at the position at which the line I-I is stopped corresponds to the time-varying spectrum in Part (B) of FIG. 17. Therefore, with the operator shifting the line I-I in Part (A) of FIG. 17 to the left or right through the operation of the operation panel 41 to change the fluorescence wavelength, the excitation spectrum in Part (B) of FIG. 17 is changed in synchronization. In this example, the line I-I in Part (A) of FIG. 17 is selecting the fluorescence wavelength of 540 nm, and the time-varying spectrum for the fluorescence wavelength of 540 nm is displayed in Part (B) of FIG. 17. Moreover, the sample images are acquired in synchronization with the measurement time, and hence it is preferred that the sample image list be displayed below the measurement time axis.

In Part (C) of FIG. 17, the fluorescence spectrum taken along the line II-II in Part (A) of FIG. 17 is displayed. The line II-II of the horizontal axis generated by the computer 31 (controller 32) and displayed by the display 42 is a selection tool for selecting a particular measurement time corresponding to a particular position along the vertical axis of the three-dimensional time-varying spectrum. With the operator operating with the use of the operation panel 41, the line II-II can be moved (slid) in the up-and-down direction (vertical direction) to select any measurement time corresponding to a stop position. The line II-II is, so to speak, a selection line for selecting the measurement time, and is sometimes called "trace bar", for example.

A cross section of the three-dimensional time-varying spectrum in Part (A) of FIG. 17 at the position at which the line II-II is stopped corresponds to the fluorescence spectrum in Part (C) of FIG. 17. Therefore, with the operator shifting the line II-II in Part (A) of FIG. 17 upward or downward through the operation of the operation panel 41 to change the measurement time, the fluorescence spectrum in Part (C) of FIG. 17 is changed in synchronization. In this example, the line II-II in Part (A) of FIG. 17 is selecting the measurement time of 300 seconds, and the fluorescence spectrum for the measurement time of 300 seconds is displayed in Part (C) of FIG. 17. Moreover, a fluorescence spectrum bar indicating a color corresponding to the fluorescence wavelength is also displayed.

In Part (D) of FIG. 17, the sample images are displayed. In this example, a white light image is displayed on the left, and a fluorescence image is displayed on the right. As the white light image, a white light image acquired before the measurement can be displayed, for example. The fluorescence image corresponds to a fluorescence image at the fluorescence wavelength and the measurement time selected by the line I-I and the line II-II in Part (A) of FIG. 17, respectively, and in this example, a fluorescence image at the fluorescence wavelength of 540 nm and the measurement time of 300 seconds is displayed.

In this example, in Part (B) of FIG. 17, a measurement time selection line (bar) L3 indicating the measurement time (300 seconds) that is being selected by the line II-II is displayed. Moreover, in Part (C) of FIG. 17, a fluorescence wavelength selection line (bar) L2 indicating the fluorescence wavelength (540 nm) that is being selected by the line I-I is displayed. Those selection lines L3 and L2 easily indicate which time or wavelength is selected for a sample image in each of the time-varying spectrum and the fluorescence spectrum to display the sample image in Part (D) of FIG. 17. It is desired that, with movements of the line I-I and the line II-II, the selection lines L3 and L2 be also moved in synchronization. Moreover, through selection of any one of the sample images in the sample image lists in Part (A) of FIG. 17 and Part (B) of FIG. 17, spectra corresponding to the selection may be displayed in Parts (A) to (C) of FIG. 17, and a fluorescence image that is enlarged to correspond to the selection may be displayed in Part (D) of FIG. 17.

Figure 18:
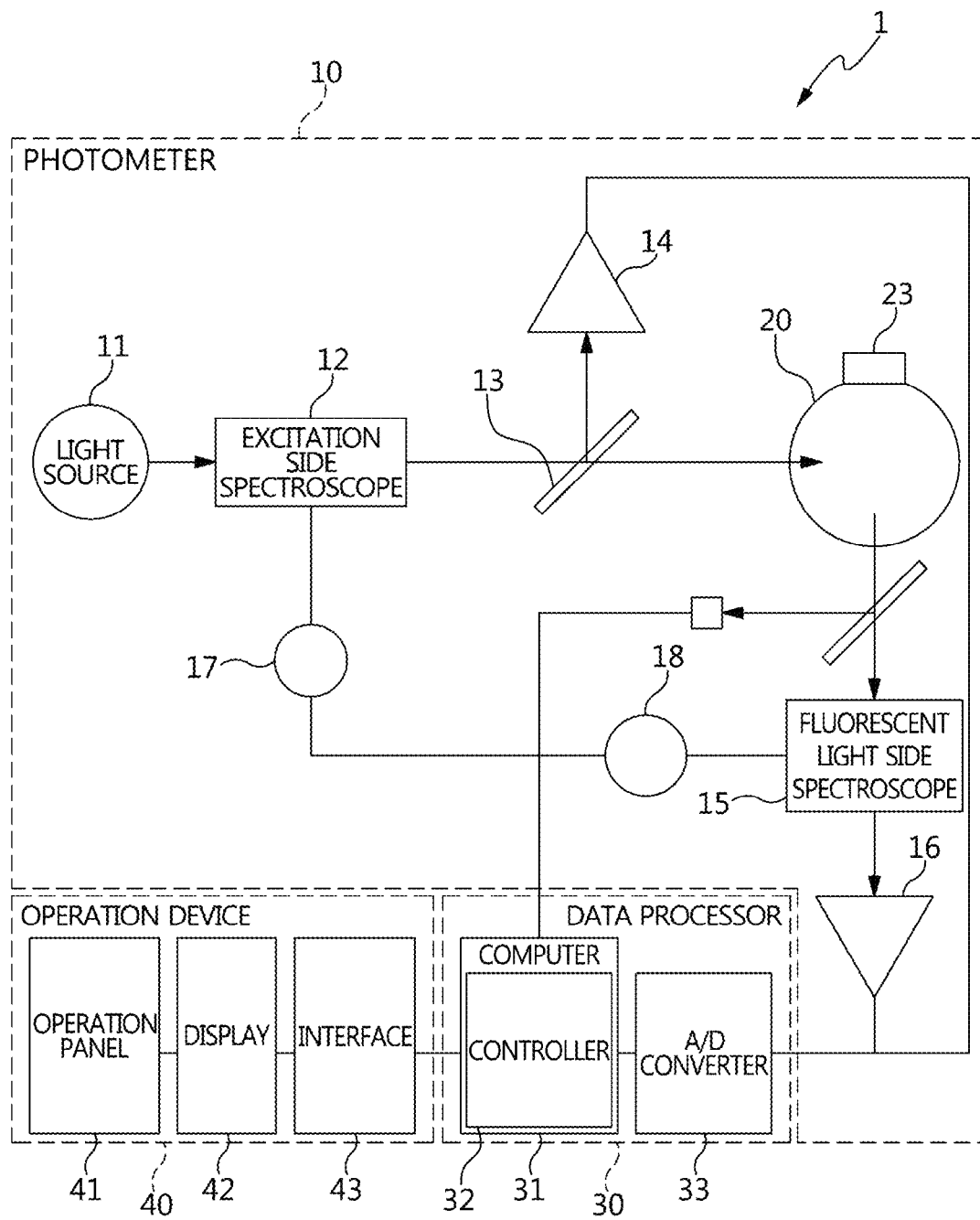
FIG. 18 is a configuration block diagram for illustrating a fluorescence spectrophotometer according to another embodiment of the present invention.
Figure 19:
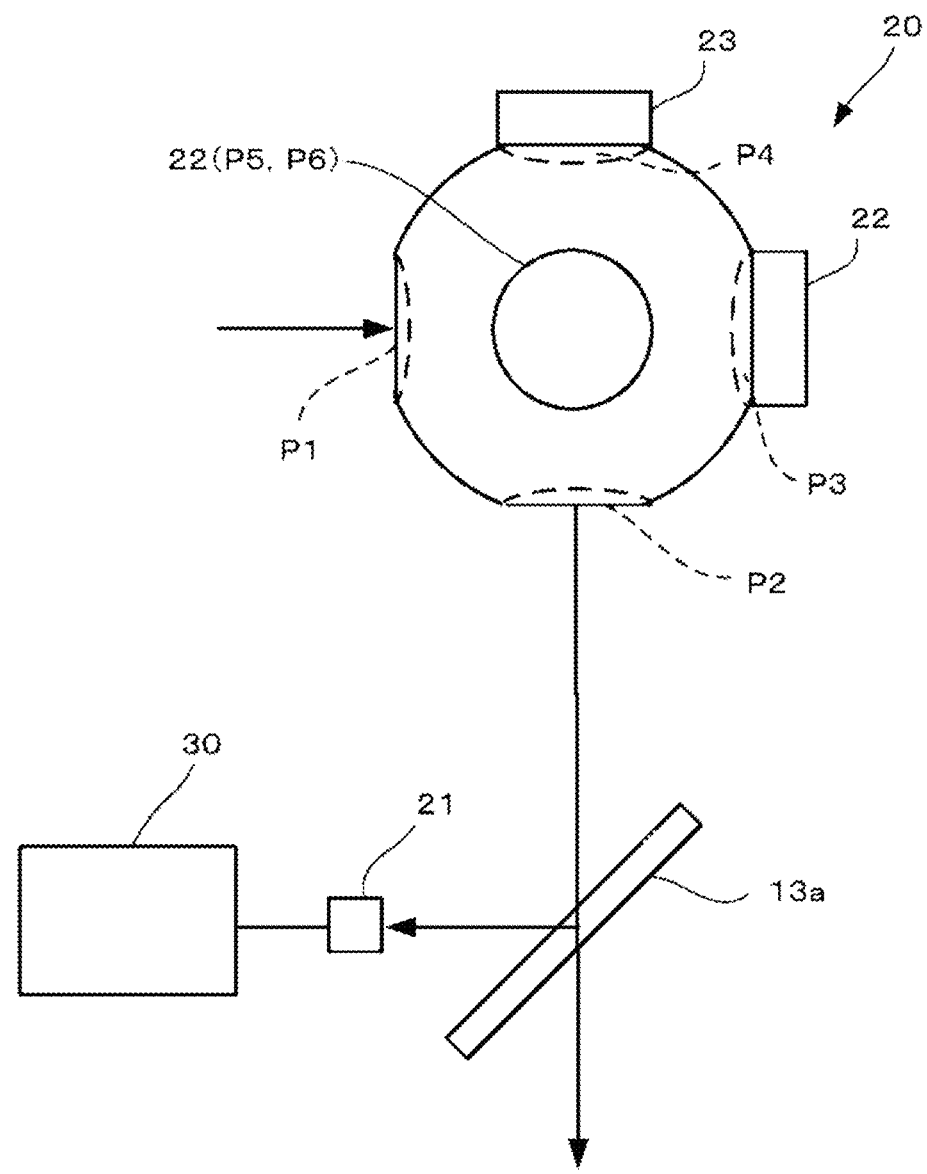
FIG. 19 is a diagram for illustrating a configuration of an integrating sphere and a camera module in the embodiment of FIG. 18.

In FIG. 18 and FIG. 19, a fluorescence spectrophotometer 1 according to another embodiment of the present invention is illustrated. Also in this embodiment, the sample holder 23 is at a position that is not directly irradiated with the excitation light, but as opposed to the configuration of FIG. 6A and FIG. 6B, is placed at a position of the port P4 of the integrating sphere 20. Further, a beam splitter 13a, which is not included in the configuration of FIG. 1, is provided at a position opposed to the port P2, which is opposite to the port P4. Then, the camera module 21 is provided not on the integrating sphere 20, but at a position at which fluorescent light that is separated by the beam splitter 13a and bent in a 90-degree direction enters the integrating sphere 20, that is, outside the integrating sphere 20. In other words, the camera module 21 captures fluorescent light that is emitted from the sample, scattered by the inner surface of the integrating sphere 20, then emitted from the integrating sphere 20, and separated by the beam splitter 13a to take a sample image.

In other words, in this configuration, as the port from which the fluorescent light is extracted and the port from which light is taken into the camera module 21, the common port P2 is used, and hence the detector 16 and the camera module 21 capture the fluorescent light that has passed through the common port P2, which is formed in the integrating sphere 20. Therefore, the number of openings in the integrating sphere 20 is two (ports P1 and P2), which is reduced from the number of openings (three ports P1, P2, and P6) in the form of FIG. 6A and FIG. 6B. A large number of openings leads to a loss of the amount of light, and hence to an increase of noise in the fluorescence spectrum and the sample image. With the use of this configuration, the number of openings, the loss of the amount of light, and the noise can be reduced. Moreover, the fluorescence spectrum and the sample image can be acquired on the same optical path.

Figure 20:
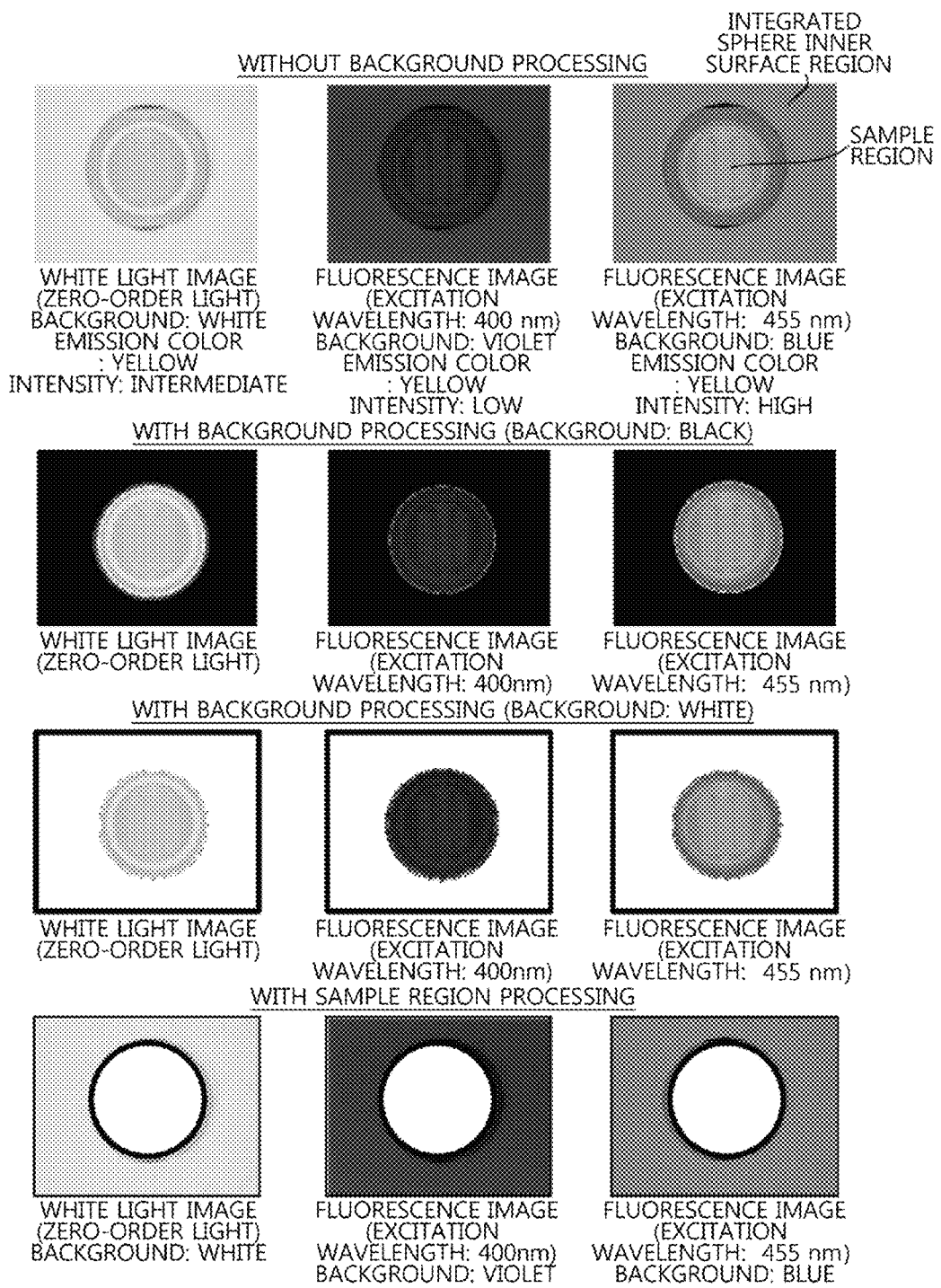
FIG. 20 is a diagram for illustrating Example relating to background processing of sample images.

In FIG. 20, there is illustrated Example relating to background processing of sample images. When the sample images are acquired by this measurement system, a sample portion and a region of the inner surface (inner wall) of the integrating sphere 20 appear in the sample images. When an image pickup element of the camera module (imaging device) 21 has a predetermined sensitivity in a visible region (visible region image pickup device), the visible range becomes a target to be photographed, and color sample images are obtained. The fluorescence spectrophotometer 1 can set ultraviolet, visible, and near-infrared regions as a target to be measured, and hence with the use of an image pickup element having a predetermined sensitivity in the ultraviolet region (ultraviolet region image pickup device) and an image pickup element having a predetermined sensitivity in the near-infrared region (near-infrared region image pickup device), sample images corresponding to those wavelength regions can also be acquired. As the image pickup element, each of the ultraviolet region image pickup device, the visible region image pickup element, and the near-infrared region image pickup element may be used alone, or a plurality of the ultraviolet region image pickup device, the visible region image pickup element, and the near-infrared region image pickup element may be used in combination depending on the purpose. When the sample is irradiated with the excitation light, reflected light of the excitation light on the sample or the fluorescent light is obtained as sample image information from the sample portion. When the sample has absorption characteristics, the portion forms an image that takes the excitation light, the fluorescent light, and the absorption into consideration due to the effect of the absorption.

Meanwhile, the inner surface of the integrating sphere 20 is covered by a white material with substantially no effect of absorption, and the portion forms an image corresponding to the monochromatic light of the excitation light. Depending on the white material on the inner surface portion of the integrating sphere, there are cases with the effect of absorption depending on the wavelength region, and in those cases, the portion forms an image that takes the effects of the reflection of the monochromatic light of the excitation light and the absorption by the white material on the inner surface of the integrating sphere 20 into consideration. The region of the sample portion (sample region) and the region of the inner surface of the integrating sphere (integrating sphere inner surface region) have different wavelength characteristics, and hence the regions form images having different brightnesses and hues. The brightness of the integrating sphere inner surface region corresponds to the intensity of the excitation light, and the hue corresponds to the wavelength of the excitation light. Therefore, the brightness and the hue are useful information. Meanwhile, when attention is to be focused on the image of the sample region, the integrating sphere inner surface region corresponds to the background region. Therefore, with a change in brightness and hue of the background that is caused when the excitation wavelength is changed, contrast illusion occurs, and it becomes difficult to accurately and visually recognize the brightness and the hue of the sample region.

To address the above-mentioned problem, the computer 31 (controller 32) sets coordinates of the sample region and coordinates of the integrating sphere inner surface region in the sample images, and based on the coordinates of the integrating sphere inner surface region, the integrating sphere inner surface region is registered as background. Then, the computer 31 (controller 32) fills background colors under different excitation wavelength conditions uniformly with a particular color, and performs the background processing in which the images after the processing are displayed by the display 42. As a result, the background colors accompanying the change in excitation wavelength can be unified, and brightnesses and hues in the sample regions can be compared without the effect of the contrast illusion. FIG. 20 is a diagram for illustrating examples in which the background color is unified to black or white (second and third rows), but the background may be any color. When brightnesses and hues in the integrating sphere inner surface regions accompanying the change in excitation wavelength are to be compared, the coordinates of the sample regions may be displayed while being filled with a uniform color (white example in the bottom row). The comparison of the background colors is facilitated.

Figure 21:
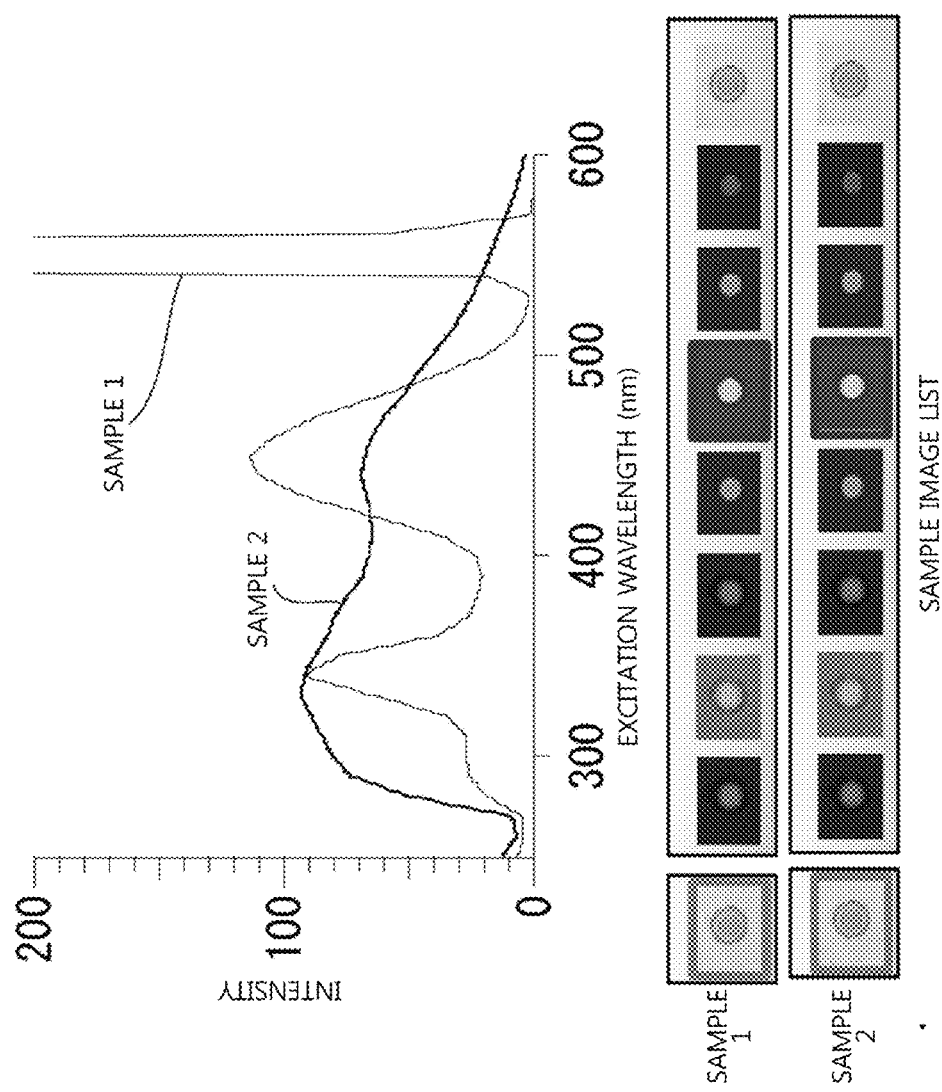
FIG. 21 is a diagram for illustrating a display example in which measurement results of excitation spectra and sample images for a plurality of samples are superimposed and displayed.
Figure 22:
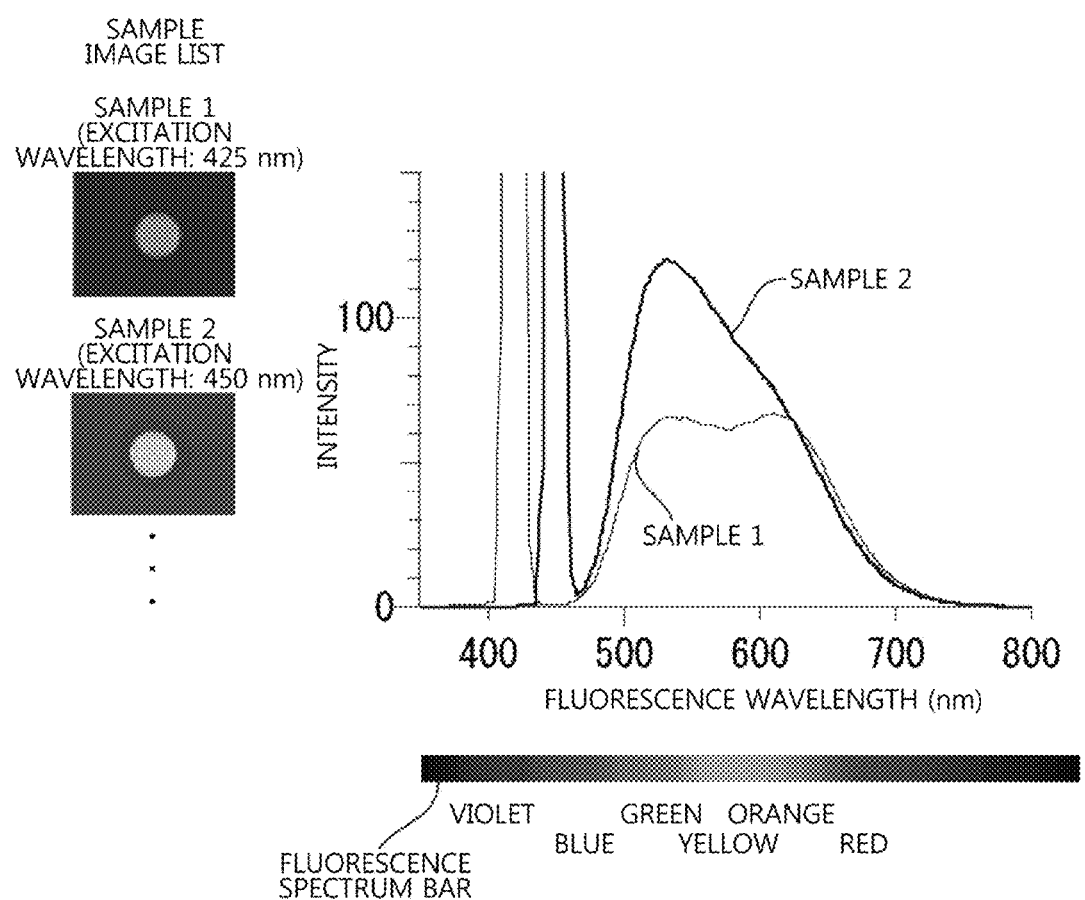
FIG. 22 is a diagram for illustrating a display example in which measurement results of fluorescence spectra and sample images for the plurality of samples are superimposed and displayed.
Figure 23:
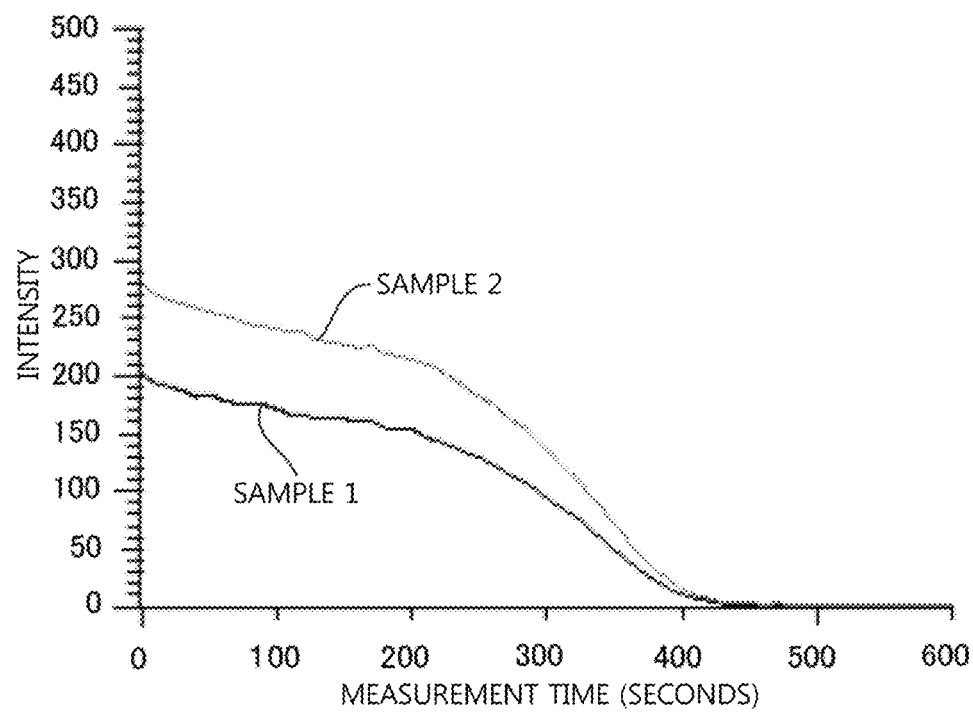
FIG. 23 is a diagram for illustrating a display example in which measurement results of time-varying spectra and sample images for the plurality of samples are superimposed and displayed.
Figure 23:
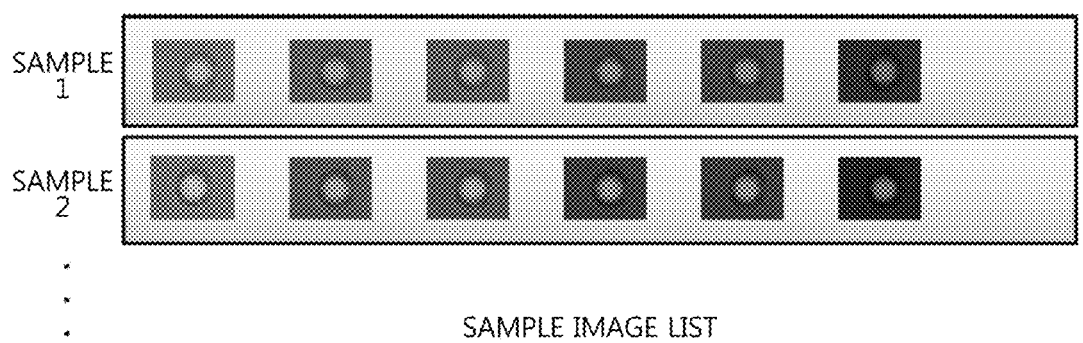

In FIG. 21 to FIG. 23, there are illustrated examples in which the display 42 displays various spectra and sample images corresponding to a plurality of samples in an arrangement in the same screen. In FIG. 21, there is illustrated a display example obtained when measurement results of excitation spectra and the sample images for the plurality of samples are superimposed and displayed. The display 42 superimposes and displays the excitation spectra for the plurality of samples, and in the sample image list, sample images at respective excitation wavelengths for each of the samples are displayed in an arrangement.

In FIG. 22, there is illustrated a display example in which measurement results of fluorescence spectra and the sample images for the plurality of samples are superimposed and displayed. The display 42 superimposes and displays the fluorescence spectra for the plurality of samples, and in the sample image list, the sample images for each of the samples are displayed in an arrangement.

In FIG. 23, there is illustrated a display example in which measurement results of time-varying spectra and the sample images for the plurality of samples are superimposed and displayed. The display 42 superimposes and displays the time-varying spectra for the plurality of samples, and in the sample image list, the sample images at respective measurement times for each of the samples are displayed in an arrangement.

Through observation of the displays of FIG. 21 to FIG. 23, the operator can easily compare various kinds of information for the plurality of samples, and can easily grasp differences in properties among the samples.

Figure 24:
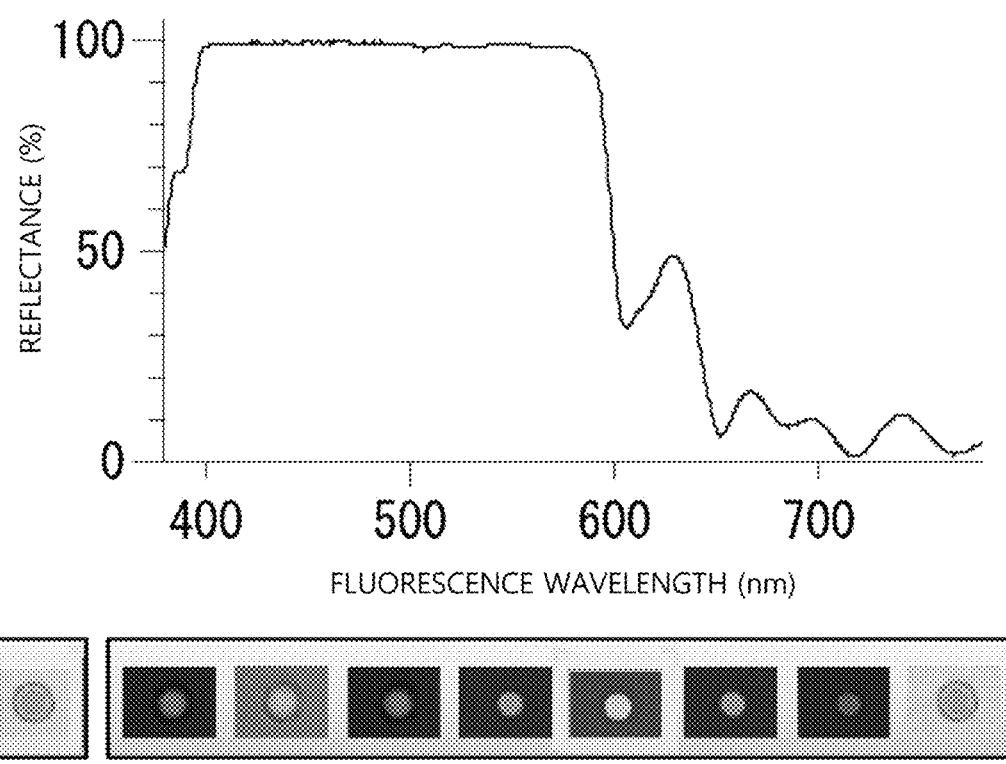
FIG. 24 is a diagram for illustrating a display example of a reflection spectrum and sample images.

In FIG. 24, a display example of a reflection spectrum and the sample images is illustrated. When the reflection spectrum is to be measured, instead of the sample holder 23 configured to hold the sample, a white material (aluminum oxide, PTFE resin plate, or the like) having a high reflectance as a reference reflector is placed on the integrating sphere 20. Then, the reference reflector is sequentially irradiated with separated light, and a base line is acquired with an amount of light at the same wavelength being set as a value of 100%. Thereafter, the sample holder 23 containing the sample is placed on the integrating sphere 20, and a change in amount of light that is reflected from the sample is ratioed with the amount of light as the base line to measure a reflectance. The display 42 displays the reflection spectrum based on the reflectance and the sample image list in an arrangement.

Figure 25A:
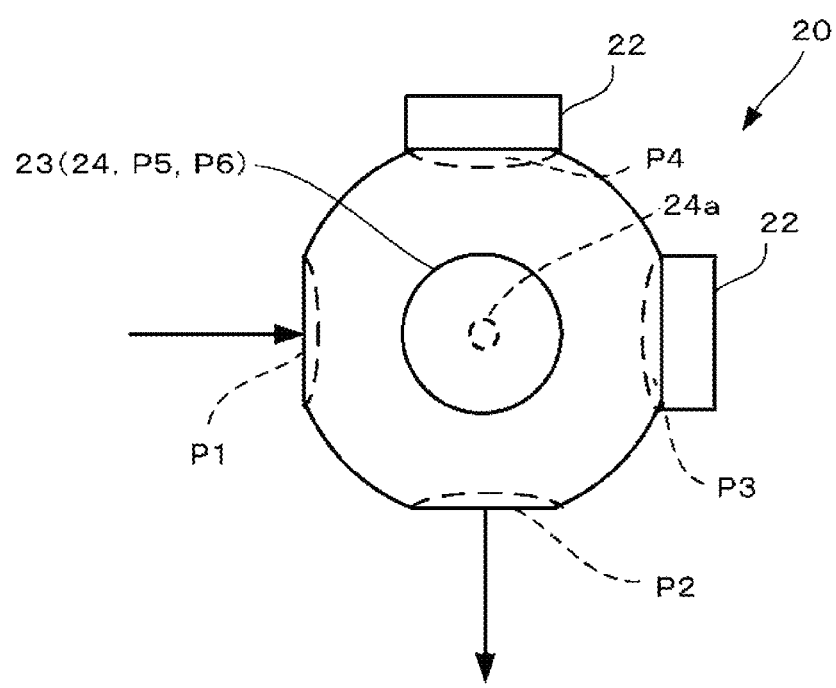
Figure 25B:
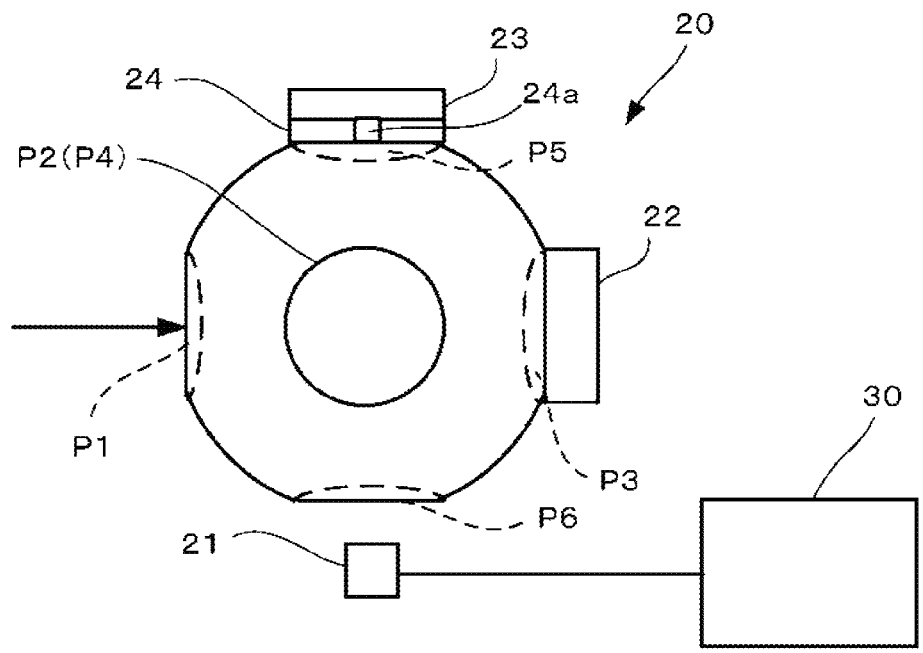

In FIG. 25A and FIG. 25B, an integrating sphere 20 according to still another example of the present invention is illustrated, which is a configuration of the integrating sphere 20 that is suitable for acquiring a sample image of a minute region. On the integrating sphere 20 in this embodiment, an aperture 24 having a flat plate shape, which is obtained by forming a hole 24a having a suitable size in a black circular plate, is placed between the sample holder 23 and the integrating sphere 20, in particular, the port P5 on which the sample holder 23 is placed. The aperture 24 has a role of partially blocking the fluorescent light emitted from the sample, and when the size (diameter) of the hole 24a of the aperture 24 becomes smaller, the amount of fluorescent light to be blocked becomes larger, and the amount of emitted fluorescent light becomes smaller. The diameter of the hole 24a of the aperture 24 can be determined depending on the fluorescence spectra and an S/N ratio of the sample image.

For example, a fluorescent material for an LED having a high fluorescence intensity emits strong fluorescent light, and hence when the integrating sphere 20 has an inner diameter φ of 60 mm, and the port P5 has a diameter φ of 20 mm, the aperture 24 may have an outer diameter φ of 20 mm, which is a size that closes the port P5, and the hole 24a formed in the center portion of the aperture 24 may have a size φ that is reduced to about 1 mm.

Figure 26:
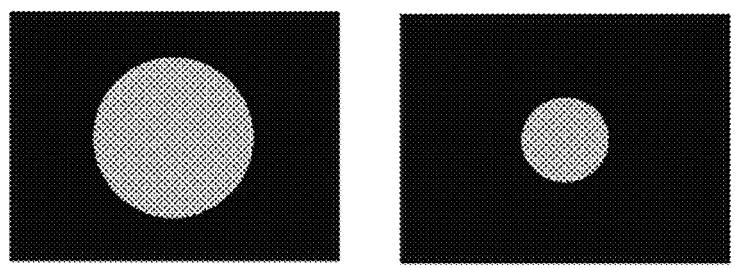
FIG. 26 is a diagram for illustrating comparison of sample images with and without an aperture of the integrating sphere.

In FIG. 26, comparison of sample images with and without the aperture 24 is illustrated. With the provision of the aperture 24, attention can be focused on the sample images of the minute region. When the fluorescent material in the sample is unevenly distributed, local information can be obtained to acquire only information on a local portion. Only the local portion is observed, and hence in a case of the same field of view, there is a disadvantage of a reduced number of pixels in the sample region. This problem is solved by using a zoom lens having a focal length that is suitable for a lens mounted in the camera module 21 depending on the size of the hole 24a of the aperture 24.

The fluorescence spectrophotometer according to the present invention has mounted therein the integrating sphere, and acquires the various spectra for the sample placed on the integrating sphere as well as the fluorescence image of the sample. The sample is placed at a position on the integrating sphere that is not directly irradiated with the excitation light, and the sample is irradiated with the excitation light that is diffusely reflected by the inner surface of the integrating sphere. As a result, with the excitation light with the reduced unevenness, the spectra and the sample images obtained based on the fluorescent light in the even state can be observed.

Further, according to the fluorescence spectrophotometer of the present invention, the controller processes the measurement data containing the various spectra indicating the intensities of the fluorescent light and the sample images, with the result that the display can display the spectra and the sample images in the same screen in the arrangement. As a result, the convenience of the measurement and the efficiency of the analysis can be further increased.

Moreover, according to the present invention, there is provided a fluorescence spectrophotometry and imaging method in which the fluorescent light is detected and the signal intensity of the fluorescent light as well as the sample images of the sample are acquired at the same time. In the method, the excitation light is allowed to enter the inner surface of the integrating sphere, the sample to be measured is irradiated with the excitation light scattered by the inner surface, the fluorescent light emitted from the sample irradiated with the excitation light is detected, and the sample images of the sample that emits the fluorescent light are taken. As a result, the convenience of the measurement and the efficiency of the analysis can be further increased.

In the above description, the measurement data that is processed by the controller 32 and displayed by the display 42 is obtained from the photometer 10, and the measurement data of the fluorescence spectrophotometer 1 is processed and displayed. However, various processing modes of the display 42 described in the embodiments are not only limited to the measurement data of the fluorescence spectrophotometer. In other words, the concept of the present invention can be applied to a general photometric analyzer configured to irradiate a sample with light to analyze the sample, and the present invention can be perceived as a display device for the photometric analyzer configured to display a measurement result of the photometric analyzer. The general photometric analyzer includes not only the fluorescence spectrophotometer but also a spectrophotometer, a fluorescence photometer, an X-ray measurement device, or other such device.

The above-mentioned display device for the photometric analyzer includes a general controller and a display configured to display an image based on measurement data processed by the controller, and the measurement data at least contains a spectrum indicating an intensity of emitted light, which is emitted by the sample irradiated with the light, and a sample image of the sample, which is taken by the imaging device. In the above-mentioned embodiments, the intensity of the emitted light corresponds to an intensity of fluorescent light. Then, as in the embodiment illustrated in FIG. 8 to FIG. 10, the display performs display of the spectrum and the sample image in the same screen in an arrangement.

As in the example illustrated in FIG. 8, the controller generates the sample image list including the plurality of sample images corresponding to the wavelengths of each of the wavelength axes of various kinds of light corresponding to the excitation wavelength axis and the fluorescence wavelength axis. The display may display the sample image list in an arrangement so that the sample image list corresponds to the wavelength axis. As in the example illustrated in FIG. 10, the controller may generate the sample image list including the plurality of sample images corresponding to the measurement times of the measurement time axis, and the display may display the sample image list in the arrangement so that the sample image list corresponds to the measurement time axis of the spectrum.

The display device for the photometric analyzer in this example can also display such a three-dimensional spectrum as illustrated in Part (A) of FIG. 11. The three-dimensional spectrum includes a first wavelength axis, a second wavelength axis, and a spectrum intensity axis. The first wavelength axis corresponds to the excitation wavelength axis in the embodiment, and corresponds to a wavelength of incident light on the sample. The second wavelength axis corresponds to the fluorescence wavelength axis in the embodiment, and corresponds to a wavelength of the emitted light from the sample. The spectrum intensity axis corresponds to an intensity of the emitted light, which is determined by the first wavelength axis and the second wavelength axis. As opposed to the first wavelength axis and the second wavelength axis, the spectrum intensity axis is not explicitly expressed in a form of an axis, but corresponds to a virtual axis that extends in a direction perpendicular to the paper surface, and in this embodiment, the contour lines corresponding to the axis are expressed.

As in the example illustrated in Part (A) of FIG. 11, the controller generates the sample image list including the plurality of sample images corresponding to the wavelengths of at least one of the first wavelength axis and the second wavelength axis, and the display displays the sample image list in the arrangement so that the sample image list corresponds to the one of the first wavelength axis and the second wavelength axis.

Moreover, the display device for the photometric analyzer in this example can also display such a three-dimensional spectrum as illustrated in Part (A) of FIG. 17. This three-dimensional spectrum includes the wavelength axis, the measurement time axis, and the spectrum intensity axis. The wavelength axis corresponds to the fluorescence wavelength axis in the embodiment, and corresponds to the wavelength of the incident light on the sample, but may correspond to the wavelength of the emitted light from the sample. The measurement time axis is the same as that in the embodiment. The spectrum intensity axis corresponds to the intensity of the emitted light, which is determined by the wavelength axis and the measurement time axis. As opposed to the wavelength axis and the measurement time axis, the spectrum intensity axis is not explicitly expressed in a form of an axis, but corresponds to a virtual axis that extends in a direction perpendicular to the paper surface, and in this embodiment, the contour lines corresponding to the axis are expressed.

As in the example illustrated in Part (A) of FIG. 17, the controller generates the sample image list including the plurality of sample images corresponding to the measurement times of the measurement time axis, but may generate the sample image list corresponding to the wavelengths of the wavelength axis. The display displays the sample image list in the arrangement so that the sample image list corresponds to any one of the wavelength axis and the measurement time axis.

Further, the display device for the photometric analyzer in this example can provide the measurement data display (integrated data display) in such an integrated form as illustrated in FIG. 11 and FIG. 17. The controller generates a first two-dimensional spectrum and a second two-dimensional spectrum respectively corresponding to Parts (B) and (C) of FIG. 11 or Parts (B) and (C) of FIG. 17. Further, the controller generates a three-dimensional spectrum, which corresponds to Part (A) of FIG. 11 or Part (A) of FIG. 17 and is formed of three axes included in the first two-dimensional spectrum and the second two-dimensional spectrum. As illustrated in FIG. 11 and FIG. 17, the display displays the first two-dimensional spectrum, the second two-dimensional spectrum, the three-dimensional spectrum, and the sample images in the arrangement in the same screen. Further, the controller generates the sample image list including the plurality of sample images corresponding to any one axis of the first two-dimensional spectrum, the second two-dimensional spectrum, and the three-dimensional spectrum, and the display can display the sample image list in the arrangement so that the sample image list corresponds to the axis.

The present invention is not limited to the embodiments described above, and modifications, alterations, and the like can be made thereto as appropriate. Other materials, shapes, dimensions, numerical values, forms, numbers, arrangement places, and the like of the components in the embodiments described above may be freely selected as long as the present invention can be achieved, and are not limited.

The fluorescence spectrophotometer and the display device for the photometric analyzer in the present invention can acquire both excellent spectra and the sample images reflecting the actual conditions of the sample, can also increase the convenience of the measurement, and can further increase the efficiency of the analysis. Therefore, the technology of analyzing the sample with the use of light is further refined.

What is claimed is:

1. A fluorescence spectrophotometer, comprising:
    a light source;
    an excitation side spectroscope configured to separate light from the light source to generate excitation light;
    an integrating sphere, which has an inner surface configured to scatter the excitation light that has entered the integrating sphere through a first port of the integrating sphere;
    a sample holder, which is provided at a position on the integrating sphere that is not directly irradiated with the excitation light that has entered the integrating sphere and that is capable of being irradiated with the excitation light that has been scattered by the inner surface, and which is capable of holding a sample to be measured;
    a detector configured to detect fluorescent light emitted from the sample irradiated with the excitation light that has been scattered by the inner surface, which is placed to a second port of the integrating sphere configured to extract the fluorescent light in a direction of 90 degrees with respect to a direction of incidence of the excitation light; and
    an imaging device configured to take a sample image of the sample that emits the fluorescent light, the imaging device placed to be opposed to a third port of the integrating sphere which is located opposite to the sample holder, the third port being spatially separate from the second port.

2. A fluorescence spectrophotometer according to claim 1, wherein the imaging device is provided at a position that is opposite to the position of the sample holder when viewed from a center of the integrating sphere, and
    wherein the imaging device is configured to directly capture the fluorescent light emitted from the sample to take the sample image.

3. A fluorescence spectrophotometer according to claim 1, wherein the imaging device is provided outside the integrating sphere, and
    wherein the imaging device is configured to capture fluorescent light that has been scattered by the inner surface and then exited from the integrating sphere to take the sample image.

4. A fluorescence spectrophotometer according to claim 3, wherein the detector and the imaging device are configured to capture fluorescent light that has passed through a common hole that is formed in the integrating sphere.

5. A fluorescence spectrophotometer according to claim 1, further comprising an aperture, which is provided between the integrating sphere and the sample holder to partially block the fluorescent light emitted from the sample.

6. A fluorescence spectrophotometer according to claim 1, further comprising a display configured to display a spectrum of an intensity of the fluorescent light, which is acquired by the detector, and the sample image in an arrangement in the same screen.

7. A fluorescence spectrophotometry and imaging method, comprising:
    allowing excitation light to enter an inner surface of an integrating sphere through a first port of the integrating sphere;
    irradiating a sample to be measured with the excitation light that has been scattered by the inner surface;
    detecting fluorescent light emitted from the sample irradiated with the excitation light using a detector which is placed at a second port of the integrating sphere configured to extract the fluorescent light in a direction of 90 degrees with respect to a direction of incidence of the excitation light; and
    taking a sample image of the sample that emits the fluorescent light using an imaging device, the imaging device placed to be opposed to a third port of the integrating sphere which is located opposite to the sample holder, the third port being spatially separate from the second port.

* * * * *